United States Patent [19]

Vieira et al.

[11] Patent Number: 5,096,781
[45] Date of Patent: Mar. 17, 1992

[54] WATER-SOLUBLE COMPOUNDS AS LIGHT STABILIZERS

[75] Inventors: Eric Vieira; Hugh S. Laver, both of Fribourg, Switzerland

[73] Assignee: Ciba-Geigy Corporation, Ardsley, N.Y.

[21] Appl. No.: 450,114

[22] Filed: Dec. 13, 1989

[30] Foreign Application Priority Data

Dec. 19, 1988 [CH] Switzerland ............... 4674/88

[51] Int. Cl.$^5$ .................. B41M 5/00; G03G 9/00
[52] U.S. Cl. .................. 428/411.1; 346/135.1; 428/195; 428/211; 430/115; 503/209
[58] Field of Search .................. 346/135.1; 428/195, 428/211; 503/209; 430/115

[56] References Cited

U.S. PATENT DOCUMENTS

| | | |
|---|---|---|
| 4,256,493 | 3/1981 | Yokoyama et al. |
| 4,446,174 | 5/1984 | Maekawa et al. ............ 428/206 |
| 4,547,405 | 10/1985 | Bedell et al. |
| 4,554,181 | 11/1985 | Cousin et al. |
| 4,659,382 | 4/1987 | Kang |
| 4,664,708 | 5/1987 | Allen |
| 4,680,332 | 7/1987 | Hair et al. |
| 4,685,968 | 8/1987 | Palmer |
| 4,705,567 | 11/1987 | Hair et al. |
| 4,877,680 | 10/1989 | Sakaki et al. |
| 4,926,190 | 5/1990 | Laver ..................... 346/1.1 |
| 5,037,979 | 8/1991 | Höhener et al. ............ 544/216 |

FOREIGN PATENT DOCUMENTS

| | | | |
|---|---|---|---|
| 224909 | 6/1987 | European Pat. Off. ....... | 428/195 |
| 262821 | 4/1988 | European Pat. Off. | |
| 50-121178 | 9/1975 | Japan .................. | 428/195 |
| 61-192778 | 8/1986 | Japan .................. | 428/195 |
| 61-192780 | 8/1986 | Japan .................. | 428/195 |
| 61-192781 | 8/1986 | Japan .................. | 428/195 |

OTHER PUBLICATIONS

G. F. Bradley et al., Soc. Electrophotography of Japan, 1988, 167.

Primary Examiner—Bruce H. Hess
Attorney, Agent, or Firm—Luther A. R. Hall

[57] ABSTRACT

Compounds of the formula I

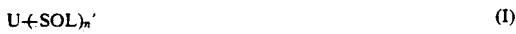

in which n' is a number from 1 to 4, U is a radical of a UV absorber of the hydroxyphenylbenzotriazole, hydroxybenzophenone, cinnamic acid or triazine type and SOL is a group of the formula Ia

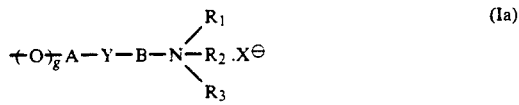

The symbols in the formula Ia are as defined in claim 1. The compounds, which are in part novel, are suitable for use as light stabilizers, particularly for recording materials and inks for ink jet printing.

2 Claims, No Drawings

WATER-SOLUBLE COMPOUNDS AS LIGHT STABILIZERS

The present invention relates to the light stabilization of recording materials for ink jet printing by the addition of water-soluble stabilizers and to novel compounds and the use thereof as stabilizers.

Printing by means of an ink jet is a printing process which can be controlled by electrical signals. In this process a fine jet of ink droplets is sprayed onto the recording material through a nozzle. The ink is a solution of a dye in an aqueous or nonaqueous solvent. The recording material should absorb the dye in the ink rapidly and permanently. In most cases specially prepared paper of plastic films provided with a dye-binding layer are used for this purpose. Owing to the fineness of the nozzles, pigments are hardly used, but dyes which are completely dissolved in the medium of the ink jet are mainly used. However, these dyes generally have a lower fastness to light than the colour pigments customary in conventional printing inks. As a result of this, recordings prepared by ink jet printing have only a limited storage life when exposed to light. When they are stored for a prolonged period in light they begin to fade or discolour. In order to solve this problem, it has been suggested, for example in U.S. Pat. No. 4,256,493, to add a water-soluble UV absorber to the ink. Anionic UV absorbers of the benzophenone class, containing sulfonate groups, were employed for this purpose, in order to ensure compatibility with the dyes in the ink, which are mostly anionic. Such benzophenone derivatives and salts thereof have the drawback in that they cause colour changes with certain dyestuffs, in particular with black dyestuffs. Furthermore, the addition of such additives can cause a reduction in the water stability of the print, since the anionic UV absorbers compete with the dye, which is also anionic, for the cationic mordant in the recording material.

A further problem in ink jet printing is the stability of the printed recording material to water, which is linked with the fastness to light. If no counter-measures, or only inadequate counter-measures, are taken, the dyes dissolve out of the recording material, when in contact with water, and bleed. Furthermore, diffusion of the dyes as a result of moisture can take place when the printed recording material is stored. This results in a reduction in the quality of the image.

It is also important that the inks, which are sprayed onto the recording material in a rapid sequence, as is the case, for example, in 4-colour ink jet printing, do not bleed into one another and produce a hazy image.

In order to solve the problem of water stability, the provision of an ink-receiving layer containing a water-soluble polymer with a content of 2 to 30% by weight of a cationic resin is suggested in DE-A 3,640,359. The cationic charges fix the dyes in the ink, which are in most cases anionic, in the ink-absorbing layer. Allowing the anionic dyes to react with a cationic polymer has already been suggested in U.S. Pat. Nos. 4,659,382, 4,664,708, 4,680,332 and 4,705,567. The insoluble product is then dispersed in the ink medium in order to impart good stability to water to the ink jet prints resulting therefrom. However, these undissolved, polymer-bound dyes increase the tendency of the ink nozzles to block.

It is known from U.S. Pat. No. 4,685,968 and EP-A 0,224,909 and 0,262,821 that replacing the Na+ ions of an anionic dye by quaternary amines. for example ammonium, quaternary alkanolamine and amidoamine ions, produces an ink having improved water stability and a reduced tendency to nozzle blockage.

All the previous suggestions for the provision of a water-resistant recording material for ink jet printing have only been obtainable at the expense of fastness to light (cf. G. F. Bradley and H. S. Laver: Fastness of Ink-Jet Prints from Water-based inks, The Soc. of Electrophotography of Japan, Japan, pages 167–169) 1988.

It has now been found that certain stabilizers containing at least one quaternary ammonium group are effective light stabilizers and are particularly suitable for stabilizing recording materials and inks, particularly for ink jet printing.

Cationic UV absorbers containing at least one quaternary ammonium group are known. Thus, for example, cationic UV absorbers of the benzotriazole type are described in JP-A 61,192,781 and 50,121,178, those of the benzophenone type are described in JP-A 61,192,778 and those of the 2-cyanocinnamic acid type are described in JP-A 61,192,780. They are used for the light stabilization of coatings, paints, dyes and cosmetics and in cationic electrodeposited paint coatings.

The present invention relates to a recording material containing, as the stabilizer, at least one compound of the formula I $$U\text{--}(SOL)_{n'} \quad (I)$$

in which n' is a number from 1 to 4, U is a radical of a UV absorber of the hydroxyphenylbenzotriazole, cinnamic acid or hydroxyphenyltriazine type, and SOL, being identical or different, is a group of the formula Ia

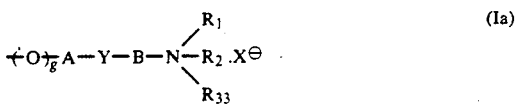

in which g is 0 or 1, A is a direct bond, $C_2$–$C_6$alkylene, $C_2$–$C_6$alkylidene or a group of the formula Ib

in which p is a number from 1 to 6, Y is a direct bond or one of the following groups:

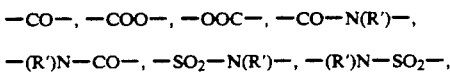

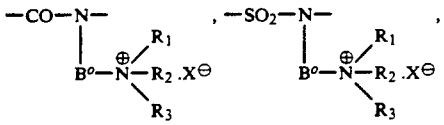

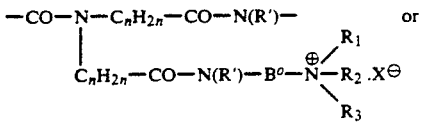

-continued

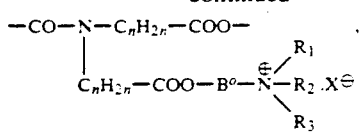

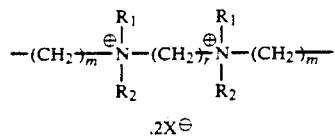

.2X$^\ominus$ where n is an integer from 1 to 4, B is a direct bond or $C_2$-$C_6$alkylene or $C_2$-$C_6$alkylidene which is unsubstituted or substituted by OH and which can be interrupted by one —O— or by one or two

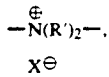

or is a group of the formulae Ic or IC

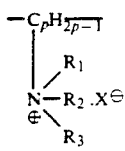         (Ic)

or

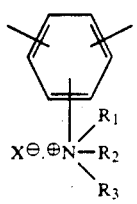         (IC)

or the group

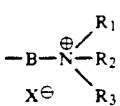

is a saturated or unsaturated mononuclear to trinuclear N-heterocyclic radical containing 1-4N atoms as ring members, at least one of which is quaternized, subject to the conditions that a) in the event that g=1, A, Y and B are not at the same time a direct bond;

b) in the event that g=1 and A=a direct bond, Y is —CO— or a direct bond; and c) in the event that B=a direct bond, Y is also a direct bond;

R' is hydrogen, $C_1$-$C_4$alkyl or $C_2$-$C_3$hydroxyalkyl, $B^o$ is —(CH$_2$)$_m$— or one of the following groups:

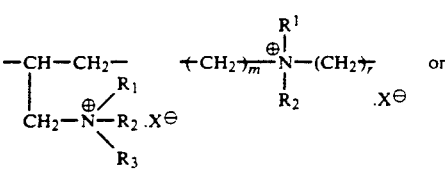

in which m and r independently of one another are 2 or 3, $R_{33}$ has one of the meanings of $R_3$ or is a group of the formulae Id and Ie

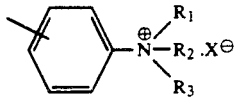         (Id)

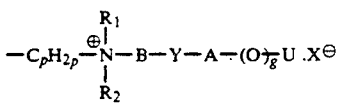         (Ie)

in which g, p, B, Y, A and U are as defined above, $R_1$, $R_2$ and $R_3$ independently of one another are hydrogen, $C_1$-$C_8$alkyl or $C_1$-$C_8$alkyl which is substituted by 1—COOR" group or by 1 to 3 OH groups, $C_2$-$C_8$hydroxyalkyl which is interrupted by one or more —O— groups, —($C_1$-$C_8$)alkylene—COO$^\ominus$, —($C_1$-$C_8$)alkylidene—COO$^\ominus$, —($C_2$-$C_8$)alkylene—SO$^\ominus_3$ or —($C_2$-$C_8$)alkylidene—SO$^\ominus_3$ each of which is substituted by one OH group, $C_3$-$C_5$alkenyl, $C_5$-$C_7$cycloalkyl, phenyl, tolyl, benzyl or glycidyl, or $R_1$, together with $R_2$ and if appropriate with $R_3$ and together with the $\overset{\oplus}{N}$ atom to which they are attached, form an N-heterocyclic radical which can contain 1-3N atoms or one O atom as ring members, R" is hydrogen or $C_1$-$C_4$alkyl and X$^\ominus$ if not present in $R_1$, $R_2$, $R_3$ or $R_{33}$, is a colourless organic or inorganic anion.

Recording materials containing a compound of the formula I in which g in the formula I is 0 and, in particular in which $R_{33}$ in the formula Ia has one of the meanings of $R_3$ are preferred. Amongst these compounds which are very particularly preferred are those in which the formula Ia corresponds to a group of the formula If

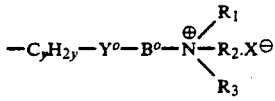         (If)

in which $Y^o$ is —COO—, —CONH— or

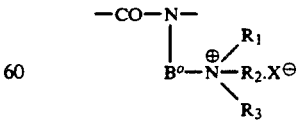

y is a number from 0 to 6 and p, $B^o$, $R_1$, $R_2$ and $R_3$ are as defined above.

Recording materials which are also preferred are those wherein the compound of the formula I is a compound of the formula II or III

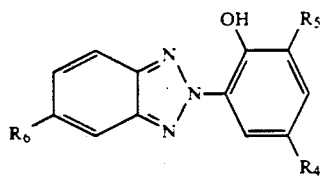

(II)

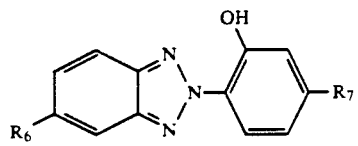

(III)

in which $R_4$ is halogen, $C_1$-$C_4$alkoxy, $C_1$-$C_8$alkyl, $C_5$-$C_6$cycloalkyl, phenyl, phenyl-$C_1$-$C_4$alkyl or a group of the formula Ia, $R_5$ and $R_6$ independently of one another are hydrogen or have one of the meanings of $R_4$, and $R_7$ is OH, $C_1$-$C_8$alkoxy which can be substituted by 1 to 3 OH groups or 1 or 2 —COOH groups, $C_1$-$C_8$alkanoyloxy, a group of the formula Ia in which g=1, or glycidyloxy, subject to the condition that at least one of $R_4$, $R_5$ and $R_6$ in the formula II and at least one of $R_6$ and $R_7$ in the formula III is a group of the formula Ia.

Compounds from this group which are particularly preferred are those in which $R_4$ is halogen, $C_1$-$C_5$alkyl, cyclohexyl or a group of the formula Ia, $R_5$ is hydrogen or has one of the meanings of $R_4$, $R_6$ is hydrogen, halogen or a group of the formula Ia and $R_7$ is OH, $C_1$-$C_4$alkoxy which is unsubstituted or substituted by 1 to 3 OH groups, glycidyloxy, $C_2$-$C_3$alkanoyloxy or a group of the formula Ia in which g=1.

Compounds which are very particularly preferred are those in which, in the formula II, $R_4$ is $C_1$-$C_4$alkyl or a group of the formula If

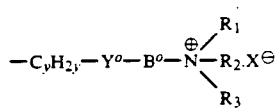

(If)

$R_5$ is hydrogen, $C_1$-$C_4$alkyl or a group If, and $R_6$ is hydrogen, Cl or the group If in which y is 0, and $B^o$, $Y^o$, $R_1$, $R_2$ and $R_3$ are as defined above, subject to the condition that at least one of $R_4$, $R_5$ and $R_6$ is a group of the formula If.

Recording materials which are also of interest are those wherein the compound of the formula I is a compound of the formula V

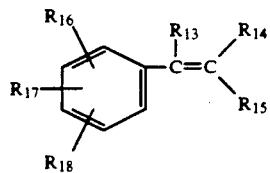

(V)

in which
$R_{13}$ is hydrogen, $C_1$-$C_8$alkyl, $C_3$-$C_8$alkenyl, phenyl-$C_1$-$C_4$alkyl or a group of the formula

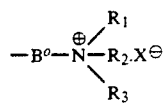

$R_{14}$ and $R_{15}$ independently of one another are —C≡N, —CO-alkyl($C_1$-$C_4$), —COO—$R_{19}$ or —CO—$NR_{20}R_{21}$, $R_{16}$, $R_{17}$, $R_{18}$, $R'_{16}$, $R'_{17}$ and $R'_{18}$ independently of one another are hydrogen, $C_1$-$C_4$alkyl, phenyl, glycidyl, OH, halogen, $C_1$-$C_4$alkoxy which is unsubstituted or substituted by 1 to 3 OH groups, or are phenoxy, benzyloxy or a group of the formula Ia and $R_{19}$, $R_{20}$ and $R_{21}$ independently of one another are hydrogen, $C_1$-$C_4$alkyl which is unsubstituted or substituted by 1 to 3 OH groups, or are $C_5$-$C_7$cycloalkyl, phenyl, benzyl, tolyl, glycidyl or a group of the formula Ig $$-B^o-\overset{\oplus}{N}\begin{matrix}R_1\\ -R_2.X^\ominus\\ R_3\end{matrix}$$ (Ig)

in which $B^o$, $R_1$, $R_2$ and $R_3$ are as defined above, subject to the condition that at least one of $R_{16}$, $R_{17}$, $R_{18}$, $R'_{16}$, $R'_{17}$ or $R'_{18}$ is a group of the formula Ia or at least one of $R_{19}$, $R_{20}$ or $R_{21}$ is a group of the formula Ig.

Recording materials which are of particular interest are those wherein the compound of the formula V is a compound of the formula Va

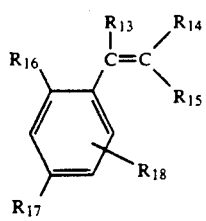

(Va)

in which $R_{13}$ is hydrogen, $C_1$-$C_4$alkyl or a group

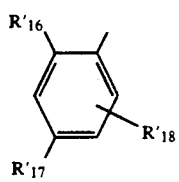

and $R_{14}$, $R_{15}$, $R_{16}$, $R_{17}$, $R_{18}$, $R'_{16}$, $R'_{17}$ and $R'_{18}$ are as defined above.

Preferred recording materials are also those wherein the compound of the formula I is a compound of the formula VI

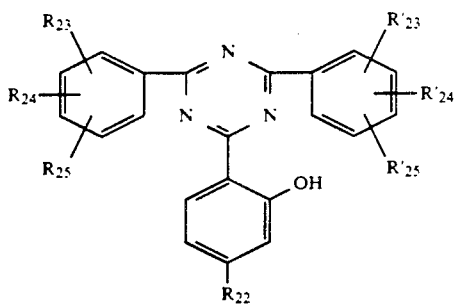

in which $R_{22}$ is a group of the formula Ia in which g is 1 and $R_{23}$, $R_{24}$, $R_{25}$, $R'_{23}$, $R'_{24}$ and $R'_{25}$ are hydrogen, OH, halogen, $C_1$-$C_4$alkoxy, $C_1$-$C_4$alkyl, phenyl or a group of the formula Ia in which g=1.

Of these, recording materials which are particularly preferred are those wherein a compound of the formula VI is a compound of the formula VIa

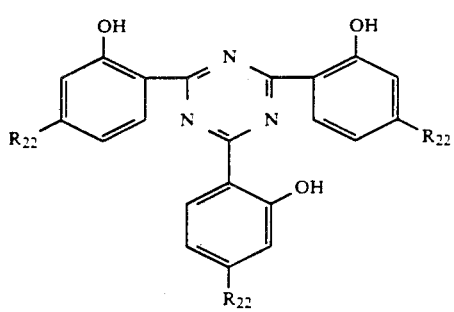

and $R_{22}$ is a group of the formula Ia in which g=1.

$X^\ominus$ in the formula Ia is preferably halogen$^\ominus$, in particular $Cl^\ominus$ or $Br^\ominus$, $C_1$-$C_4$alkyl-$COO^\ominus$, $C_1$-$C_4$alkyl-$OSO^\ominus_3$ or $R^o$-$SO^\ominus_3$ in which $R^o$ is methyl, tolyl or —$CF_3$.

Possible examples of alkyl radicals as $C_1$-$C_4$alkyl are methyl, ethyl, n-propyl, isopropyl, n-butyl, sec-butyl or t-butyl.

In addition to the meanings mentioned, possible examples of alkyl radicals as $C_1$-$C_8$alkyl are n-pentyl, t-amyl, n-hexyl, n-heptyl, 2-ethylhexyl, n-octyl or 1,1,3,3-tetramethylbutyl.

Examples of R' as $C_2$-$C_3$hydroxyalkyl are 2-hydroxyethyl or 2-hydroxypropyl.

In addition to the meanings of R', possible examples of radicals as $C_1$-$C_8$alkyl which is unsubstituted or substituted by 1 to 3 OH groups are hydroxymethyl, 3-hydroxybutyl, 2,3-dihydroxypropyl, 2,2-di(hydroxymethyl)-propyl, 4-hydroxybutyl, 6-hydroxyhexyl, 8-hydroxyoctyl, 1,2,4-trihydroxybut-2-yl, 1,2,6-trihydroxyhex-2-yl or 1,2,3-trihydroxyprop-2-yl.

Examples of $R_1$, $R_2$ and $R_3$ or $R_{33}$ as $C_2$-$C_8$hydroxyalkyl which is interrupted by one or more —O— groups are 4-hydroxy-3-oxapropyl, 5-hydroxy-3-oxapentyl, 8-hydroxy-3,6-dioxaoctyl or 11-hydroxy-3,6,9-trioxaundecyl.

Examples of B as $C_2$-$C_6$alkylene or $C_2$-$C_6$alkylidene are ethylene, ethylidene, trimethylene, tetramethylene, pentamethylene, hexamethylene, 1,2-propylene, 2,2-propylidene, 2,2-butylidene, 1,2-butylene or 2,2-dimethyl-1,3-propylene.

In addition to the meanings of B, A as $C_1$-$C_6$alkylene or $C_1$-$C_6$alkylidene can also be methylene.

If $R_1$, $R_2$ and $R_3$ are —($C_2$-$C_8$)-alkylene-$SO_3^-$, the alkylene radical can be as defined for B and can also be heptamethylene, octamethylene or 3,3-dimethyl-1,5-pentylene.

Possible examples of alkoxy radicals are methoxy, ethoxy, isopropoxy, butoxy, t-butoxy, n-hexoxy, 2-ethylhexyloxy or n-octyloxy.

Possible examples of phenyl-$C_1$-$C_4$alkyl radicals are benzyl, 2-phenylethyl, 1-phenylethyl, 3-phenylpropyl or 2-phenylprop-2-yl.

If the group

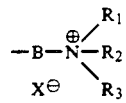

is an N-heterocyclic radical, the following are examples of possible heterocyclic radicals:

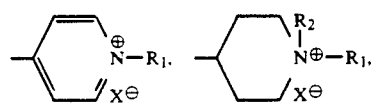

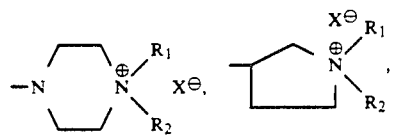

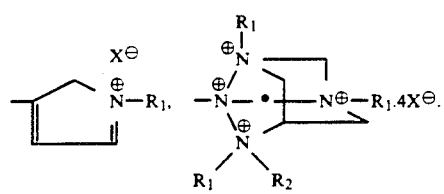

If $R_1$ and $R_2$, if appropriate together with $R_3$, are an N-heterocyclic radical, the following are examples of possible heterocyclic radicals:

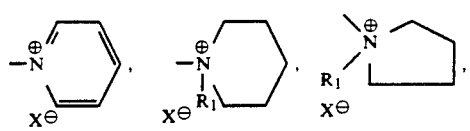

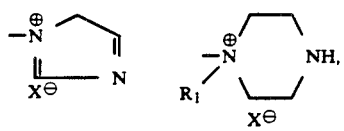

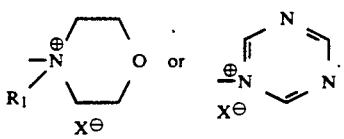

If $R_1$, $R_2$ and $R_3$ are $C_1$-$C_8$alkyl which is substituted by —COOR", the alkyl moiety can have the meaning of A as $C_1$-$C_6$alkylene or $C_1$-$C_6$alkylidene and, in addition, heptamethylene, octamethylene, 3-methyl-1,1-butylidene or 2-methyl-1,1-butylidene.

As $C_2$-$C_6$alkylene or $C_2$-$C_6$alkylidene which is unsubstituted or substituted by OH and which can be interrupted by one —O— group or by one or two —N̈(R')$_2$— groups, B is a radical in which at least two C atoms are located between two hetero atoms, for example 3-oxa-1,5-pentylene, 4-oxa-1,7-heptylene, 3-oxa-2,4-dimethyl-1,5-pentylene, 2-hydroxy-1,3-propylene, 3-hydroxy-1,5-pentylene, 4-hydroxy-1,6-hexylene, quaternized 3-aza-1,5-pentylene, 4-aza-1,7-heptylene, 2,5-diaza-1,6-hexylene, 2,5-diaza-1,7-heptylene, 3,5-diaza-1,6-hexylene or 3,6-diaza-1,8-octylene, 4-oxa-2,6-dihydroxy-1,7-heptylene, 3-oxa-5-hydroxy-1,6-hexylene, quaternized 3,6-diaza-5-hydroxy-1,8-octylene or 2-hydroxy-4-aza-1,7-heptylene.

As —($C_1$-$C_8$)-alkylene-COO$^\ominus$ or —($C_1$-$C_8$)-alkylidene-COO$^\ominus$ each of which is substituted by one OH, $R_1$, $R_2$ and $R_3$ are, for example, 1-hydroxy-3-carboxypropylene, 2-hydroxy-4-carboxybutylene, 1-carboxy-2-hydroxyethyl-1-idene, 1-carboxy-2-hydroxypropyl-1-idene or 2-hydroxy-8-carboxyoctylene.

Examples of $R_1$, $R_2$ and $R_3$ as $C_3$-$C_5$alkenyl are allyl, methallyl, n-but-2-enyl, 2-methylprop-2-enyl or n-pent-2-enyl. Possible $C_3$-$C_8$alkenyl radicals can, in addition, be n-hexenyl, n-heptenyl, n-octenyl or 2,5-dimethyl-3-hexenyl.

Possible examples of cycloalkyl radicals as $C_5$-$C_7$cycloalkyl are cyclopentyl, cyclooctyl, cyclohexyl or cycloheptyl.

The following examples of compounds of the formula I illustrate the invention:

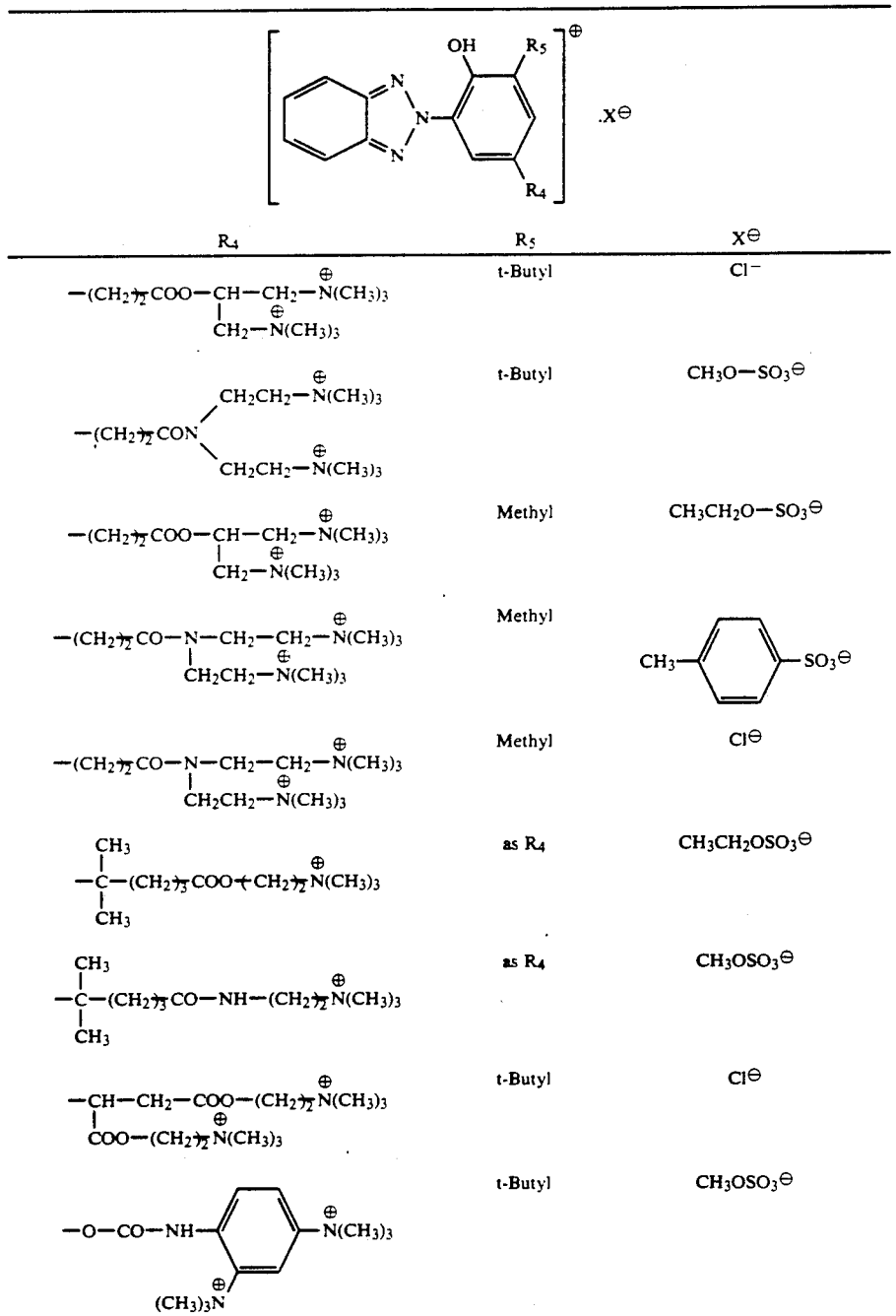

-continued

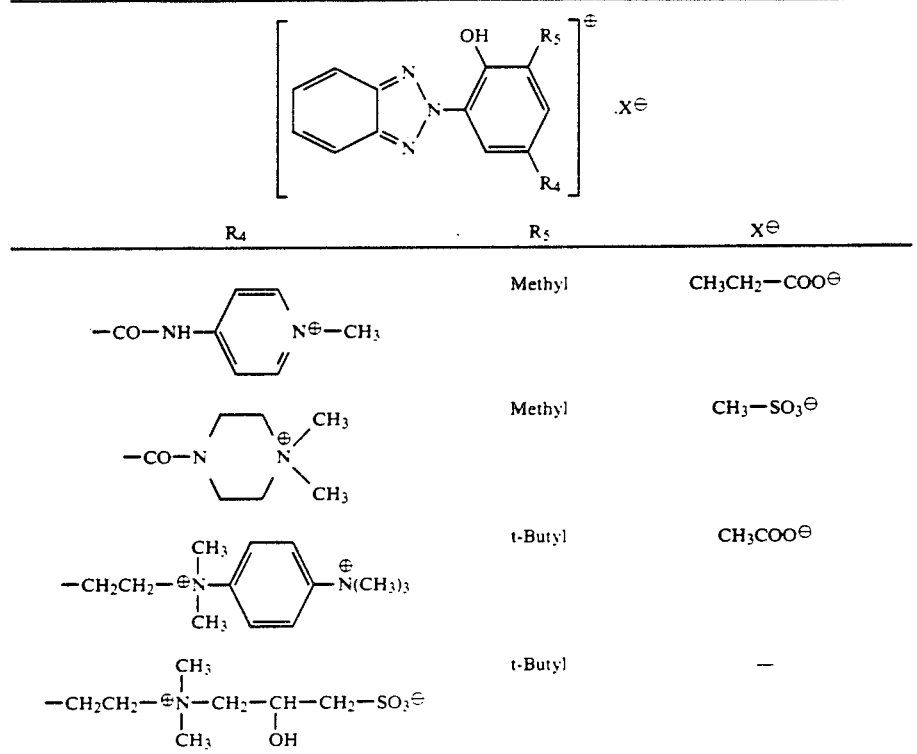

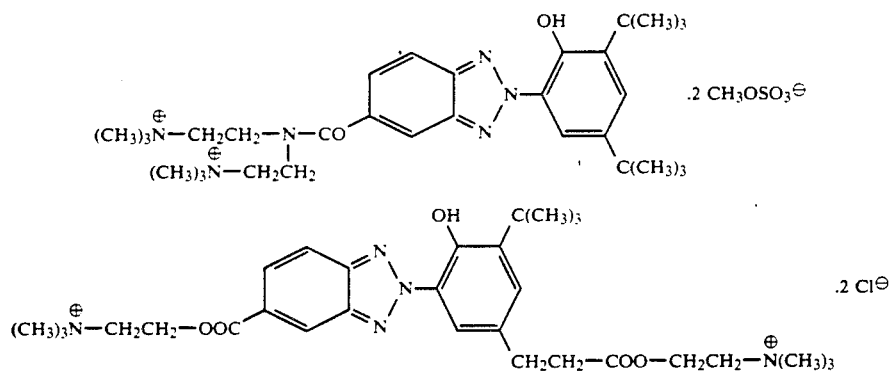

Other examples:

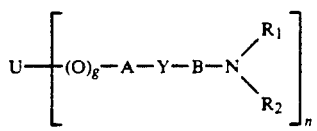

The water-soluble compounds of the formula I can, for example, be prepared by quaternizing 1 molar equivalent of a compound of the formula Ih $$U\!-\!\!\left[\!(O)_g\!-\!A\!-\!Y\!-\!B\!-\!N\!\!\begin{array}{c}R_1\\ \\R_2\end{array}\right]_n \quad \text{(Ih)}$$

with n molar equivalents of a quaternizing agent of formula $R_{33}$-X, U, A, Y, B, $R_1$, $R_2$, $R_{33}$, X, g and n being as defined above.

The quaternization can be carried out at temperatures from 0°–180°, preferably at 30°–140° C.

The following are examples of compounds suitable for use as quaternizing agents $R_{33}$-X: alkyl halides, such as methyl chloride, ethyl bromide, butyl bromide or benzyl chloride, dialkyl sulfates, such as dimethyl or diethyl sulfate, sulfonic acid esters, such as methyl or ethyl toluenesulfonate or methyl or ethyl benzenesulfonate, or epichlorohydrin, alkyl chlorides being particularly preferred.

The quaternization by means of alkyl halides, dialkyl sulfates or sulfonic acid esters to give the compounds of the formula I is preferably carried out in a solvent or solvent mixture which is inert towards the quaternizing agent. Examples of suitable solvents are hydrocarbons, such as benzene, toluene and xylene, halogenated aliphatic or aromatic hydrocarbons, such as methylene chloride, chloroform, ethylene chloride, chlorobenzene and dichlorobenzene, alcohols, such as ethanol, butanol and ethylene glycol, ethers, such as ethylene glycol monomethyl ether, ethylene glycol dimethyl ether and dioxane, amides, such as dimethylformamide and n-methylpyrrolidone, or ketones, such as acetone.

Quaternization by means of epichlorohydrin is carried out at the temperatures mentioned in an acid medium, advantageously in the presence of an organic acid, such as formic acid, acetic acid, propionic acid or benzoic acid, but inorganic acids, such as sulfuric acid, phosphoric acid or hydrogen halide acids, can also be used for this purpose. These inorganic acids can be used in a concentrated, commercially available form as dilute aqueous solutions or as a mixture with the organic solvents mentioned, if appropriate with the addition of water. If the reaction is carried out in the presence of organic acids, the concentrated form of these acids is used in most cases, if appropriate as a mixture with the organic solvents mentioned.

The starting compounds of the formula Ih are in part available commercially or can be prepared by known methods.

The recording materials according to the invention are suitable for pressure-sensitive copying systems, photocopying systems using microcapsules, heat-sensitive copying systems, photographic materials and, preferably, ink jet printing.

The recording materials according to the invention are distinguished by an unexpected improvement in quality. The ink jet printing can be carried out without coagulation of the pouring material, and the fastness to light and washing is improved at the same time.

The recording materials according to the invention have the construction known for the particular use. They consist of a customary carrier, for example paper or plastic film, which has been coated with one or more layers. Depending on the type of the material, these layers contain the appropriate necessary components, in the case of photographic materials, for example, silver halide emulsions, dye couplers, dyes and the like. Material particularly suitable for ink jet printing has a layer particularly absorptive for ink on a customary carrier.

Uncoated paper can also be employed for ink jet printing. In this case the paper acts at the same time as the carrier material and as the ink-absorbent layer.

The recording material can also be transparent, as in the case of projection films.

The compounds of the formula I can be incorporated into the carrier material as early as the production of the latter, in the production of paper, for example, by being added to the paper pulp. A second method of application is to spray the carrier material with an aqueous solution of compounds of the formula I.

In most cases, however, a dye-affinitive layer is applied to the carrier material and in this case the compounds of the formula I are added to this coating composition. The coating compositions usually consist of a solid filler and a binder as well as minor amounts of additives.

The filler is the main constituent of the coating composition in terms of quantity. Examples of suitable fillers are silica, kaolin, talc, clay, Ca, Mg or Al silicates, gypsum, zeolite, bentonite, diatomaceous earth, vermiculite, starch or the surface-modified silica described in JP-A-60-260,377. Small amounts of white pigments, for example titanium dioxide, barytes, magnesium oxide, limestone, chalk or magnesium carbonate, can be used in the coating composition together with the filler, provided that they do not reduce the density of the ink jet printing too greatly.

Coating compositions intended for transparent recording materials suitable for projection cannot contain any particles which scatter light, such as pigments and fillers.

The binder binds the fillers to one another and to the carrier material. Examples of customary binders are water-soluble polymers, for example polyvinyl alcohol, partially hydrolyzed polyvinyl acetate, cellulose ethers, polyvinylpyrrolidone and copolymers thereof, polyethylene oxide, salts of polyacrylic acid, sodium alginate, oxidized starch, gelatine, casein, vegetable gum, dextrin, albumin, dispersions of polyacrylates or acrylate-/methacrylate copolymers, latices of natural or synthetic rubber, poly(meth)acrylamide, polyvinyl ethers, polyvinyl esters, copolymers of maleic acid, melamine resin, urea resins or chemically modified polyvinyl alcohols, such as are described in JP-A-61-134,290 or 61-134,291.

Although the compounds of the formula I impart fastness to washing to the ink jet print, an additional dye receptor or a mordant, which fix the dye more firmly on the coating, can be added to the binder. Dye receptors for acid dyes are of a cationic or amphoteric nature. Examples of cationic receptors are polymeric ammonium compounds, for example polyvinylbenzyltrimethylammonium chloride, polydiallyldimethylammonium chloride, polymethacryloxyethyldimethylhydroxyethylammonium chloride, polyvinylbenzylmethylimidazolium chloride, polyvinylbenzylpicolinium chloride or polyvinylbenzyltributylammonium chloride. Other examples are basic polymers, for example poly-(dimethylaminoethyl) methacrylate, polyalkylenepolyamines and condensation products thereof with dicyandiamide, amine/epichlorohydrin polycondensates or the compounds described in JP-A 5,736,692, 5,764,591, 57,187,289, 57,191,084, 58,177,390, 58,208,357, 5,920,696, 5,933,176, 5,996,987, 59,198,188, 6,049,990, 6,071,796, 6,072,785, 60,161,188, 60-187,582, 60-189,481, 60,189,482, 6,114,979, 6,143,593, 6,157,379, 6,157,380, 6,158,788, 6,161,887, 6,163,477, 6,172,581, 6,195,977, 61,134,291 or in U.S. Pat. Nos. 4,547,405 and 4,554,181 and in DE-A 3,417,582. Gelatine is an example of amphoteric dye receptors.

The dye-binding coating can contain a number of other additives, for example antioxidants, light stabilizers (including also UV absorbers which do not belong to the UV absorbers according to the invention), viscosity improvers, fluorescent brighteners, biocides and/or antistatic agents.

Examples of suitable antioxidants are, in particular, sterically hindered phenols and hydroquinones, for example the antioxidants listed in GB-A 2,088,777 or JP-A 6,072,785, 6,072,786 and 6,071,796.

Examples of suitable light stabilizers are, in particular, organic nickel compounds and sterically hindered amines, for example the light stabilizers mentioned in JP-A 58,152,072, 61,146,591, 61,163,886, 6,072,785 and 61,146,591 or in GB-A 2,088,777, JP-A 59,169,883 and 61,177,279.

Other UV absorbers can certainly be added to the coating composition for ink jet printing, for example UV absorbers such as are described in Research Disclosure No. 24,239 (1984) p. 284, GB-A 2,088,777 and EP-A 0,280,650.

In most cases, however, by virtue of the high fastness to light imparted by the compounds of the formula I, it is possible to dispense with an additional UV absorber.

In order to ensure good dispersion of the fillers and additives, or to influence the pouring properties or the rheology of the coating compositions, it is possible to add surfactants to the latter. Suitable surfactants are only those of a nonionic, amphoteric or cationic nature, but not anionic surfactants, since the compounds of the formula I are themselves cationic.

Examples of nonionic surfactants are esters or ethers of polyethylene oxides or polypropylene oxides or copolymers thereof, fatty acid alkanolamides, ethoxylated alkanolamides, partial fatty acid esters of polyols (for example of glycerol, polyglycerol. sorbitol, pentaerythritol or sucrose), N-alkylmorpholines or long-chain amine oxides.

Examples of amphoteric surfactants are fatty acid amidoalkylbetaines, fatty acid amidoalkylsultaines, fatty acid imidazolinebetaines, N-alkyl-$\beta$-aminopropionic acids or alkylene-bis-(amidoalkylglycinates).

Examples of cationic surfactants are the quaternary ammonium salts of long-chain fatty amines and benzylamines, imidazolinium, pyridinium, picolinium or morpholinium salts having long-chain alkyl radicals, quaternary ammonium salts of long-chain alkylamidoalkylamines or bis-ammonium salts of quaternary diamines.

The coating composition is usually prepared as follows: the water-soluble components, for example the binder, are dissolved in water and stirred together. The solid components, for example fillers and other additives already described, are dispersed in this aqueous medium. Dispersion is advantageously carried out by means of devices, for example ultrasonic samples, turbine stirrers, homogenizers, colloid mills, bead mills, sand mills, high-speed stirrers and the like.

It is a particular advantage of the compounds of the formula I that they can be incorporated easily into the coating composition. Since they are water-soluble, the compounds of the formula I can be simply added to the binder solution or stirred without further treatment into the coating composition. The communication process or emulsification process, such as is necessary in the case of the conventional UV absorbers, is omitted in this case.

The coating composition is applied to the carrier, which is paper in most cases, and is dried by heating. As already mentioned, the compounds of the formula I can also be applied in the form of an aqueous solution to the recording material in a separate operation, on their own or together with other components, already described. Application can be effected by spraying, by bonding in a bonding press, by a separate pouring process or by immersion in a tub. After such an after-treatment of the recording material, an additional drying process is of course necessary.

The process for the production of the recording material, stabilized against damage by light, for ink jet printing is also a subject of the present invention and comprises coating a two-dimensional carrier with a coating composition containing at least one compound of the formula I. This recording material does not only have a good absorption capacity for ink jet printing inks, it also imparts a high fastness to light and water stability to the dye which is printed on.

The recording material prepared in this way preferably contains 1 to 5000 mg/m$^2$, in particular 50–1200 mg/m$^2$, of a compound of the formula I.

With the recording materials according to the invention, the nature of the ink and the dye dissolved in it and the nature of the printer used are immaterial.

In the case of the printers used nowadays, a distinction is drawn between those having a continuous ink jet and drop-on-demand printers, particularly bubble-jet printers. The recording material according to the invention can be used for processes based on all these types of apparatus.

The inks are in most cases aqueous inks, but they can also be solutions of the dye in an organic solvent or in a melted wax. In most cases aqueous inks also contain water-soluble solvents, for example mono-, di-, tri- or higher ethylene glycols, propylene glycol, 1,4-butanediol, or ethers of such glycols, thiodiglycol, glycerol and ethers and esters thereof, polyglycerol, mono-, di- and tri-ethanolamine, propanolamine, dimethylformamide, dimethyl sulfoxide, dimethylacetamide, N-methylpyrrolidone, 1,3-dimethylimidazolidone, methanol, ethanol, isopropanol, n-propanol, diacetone alcohol, acetone, methyl ethyl ketone or propylene carbonate.

Aqueous inks contain water-soluble dyes such as are also known for dyeing natural fibres. These can be, for example, monoazo, disazo or polyazo dyes or reactive dyes, triphenylmethane dyes, xanthene dyes or phthalocyanine dyes. Examples of these are C.I. Food Black 2, C.I. Direct Black 19, C.I. Direct Black 38, C.I. Direct Black 168, C.I. Sulphur Black 1, C.I. Acid Red 35, C.I. Acid Red 249, C.I. Direct Red 227, C.I. Acid Yellow 23, C.I. Direct Yellow 86, C.I. Acid Blue 9, C.I. Direct Blue 86 or C.I. Direct Blue 199, C.I. Acid Red 14, C.I. Acid Red 52, C.I. Reactive Red 40, C.I. Direct Yellow 107 and C.I. Direct Black 154.

Aqueous inks can also contain various additives in minor amounts, for example binders, surfactants, biocides, corrosion inhibitors, sequestering agents, pH buffers or conductivity additives. They can also contain anionic, water-soluble UV absorbers or other water-soluble light stabilizers. In general, however, the addition, in accordance with the invention, of a UV absorber to the recording material is sufficient.

If the ink is a nonaqueous ink, it is a solution of the dye in an organic solvent or solvent mixture. Examples of solvents used for this purpose are alkylcarbitols, alkylcellosolves, dialkylformamides, dialkylacetamides, alcohols, in particular alcohols having 1–4 C atoms, acetone, methyl ethyl ketone, diethyl ketone, methyl isobutyl ketone, diisopropyl ketone, dibutyl ketone, dioxane, ethyl butyrate, ethyl isovalerate, diethyl malonate, diethyl succinate, methyl pelargonate, butyl acetate, triethyl phosphate, ethyl glycol acetate, toluene, xylene, tetralin or petroleum fractions. Examples of solid waxes as solvents are stearic or palmitic acid.

Solvent-based inks of this type contain dyes soluble therein, for example Solvent Red, Solvent Yellow, Solvent Orange, Solvent Blue, Solvent Green, Solvent violet, Solvent Brown or Solvent Black. Inks of this type too can also contain further additives, for example binders, antioxidants or biocides.

As already mentioned, the recording materials according to the invention embrace a wide field. The compounds of the formula I can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microscapsules which are developed by means of pressure are described in U.S. Pat. Nos. 4,416,966, 4,483,912, 4,352,200, 4,535,050, 4,5365,463, 4,551,407, 4,562,137 and 4,608,330 and also in EP-A 139,479, EP-A 162,664, EP-A 164,931, EP-A 237,024, EP-A 237,025 or EP-A 260,129. In all these systems the compounds of the formula I can be put into the dye-receiving layer. The compounds of the formula I can, however, also be put into the donor layer in order to protect the colour formers from light.

Photographic materials which can be stabilized are photographic dyes and layers containing such dyes or precursors thereof, for example photographic paper and films. The compounds of the formula I act here as antistatic agents which increase the conductivity of the gelatin layer, and, at the same time, as a UV filter against electrostatic flashes. In colour photographic materials couplers and dyes are also protected against photochemical decomposition.

The compounds of the formula I can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, they can be employed in recording materials for dye diffusion transfer printing, thermal wax transfer printing and dot matrix printing and for use with electrostatic, electrographic, electrophoretic, magnetographic and laser-electrophotographic printers and pen-plotters.

The compounds of the formula I can also be employed in inks, preferably for ink jet printing. In this case the resistance of the ink jet print to water is improved surprisingly. This fact is probably due to the formation of a sparingly soluble salt from the anionic dye and the cation stabilizer of the formula I. It has been found that aqueous ink jet printing inks can be prepared from one or more anionic dyes and one or more compounds of the formula I, particularly if either the anionic or the cationic component is present in an adequate excess.

A further subject of the present invention is, therefore, an ink containing at least one compound of the formula I as a stabilizer.

The ink, particularly for ink jet printing, preferably contains water. Inks containing the stabilizer of the formula I in a concentration of 0.01 to 20% by weight, particularly 0.5 to 10% by weight, are also preferred.

Compounds of the formula I which have been indicated as preferred for the recording materials described above are also preferred in the inks according to the invention.

The compounds of the formula I in the recording materials according to the invention are in part novel and are therefore also a subject of the present invention.

The invention therefore relates to compounds of the formula I°

   (I°)

in which n is a number from 1 to 4, U is a radical of a UV absorber of the hydroxyphenylbenzotriazole, cinnamic acid or hydroxyphenyltriazine type, and SOL°, being identical or different, is a group of the formula I°a

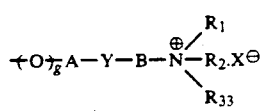

in which g is 0 or 1, A is a direct bond, $C_2$–$C_6$alkylene, or a group of the formula I°b

   (I°b)

in which p is a number from 1 to 6, Y is a direct bond or one of the following groups:

$-CO-$, $-COO-$, $-OOC-$, $-CO-N(R')-$, $-(R')N-CO-$, $-SO_2-N(R')-$, $-(R')N-SO_2-$,

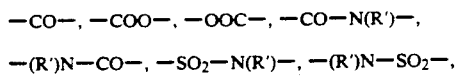

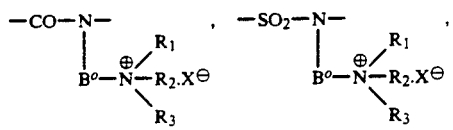

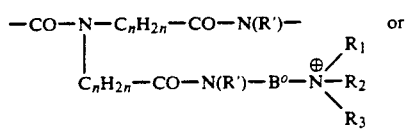

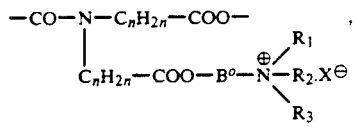

B is a direct bond or $C_2$–$C_6$alkylene which is unsubstituted or substituted by OH and which can be interrupted by one $-O-$ or by one or two $-N(R')_2-$, or is a group of the formulae I°c or I°C

   (I°c)

   (I°C)

or the group

   (I°d)

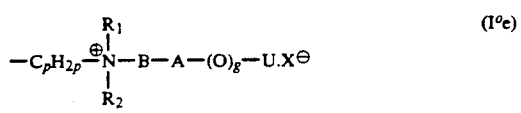   (I°e)

is a saturated or unsaturated mononuclear to trinuclear N-heterocyclic radical containing 1–4N atoms as ring members, at least one of which is quaternized, subject to the conditions that a) in the event that g=1, A, Y and B are not at the same time a direct bond;
b) in the event that g—=1 and A=a direct bond, Y is —CO— or a direct bond; and
c) in the event that B=a direct bond, Y is also a direct bond;

R' is hydrogen, C₁-C₄alkyl or C₂-C₃hydroxyalkyl, B° is —(CH₂)ₘ— or one of the following groups:

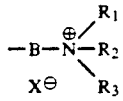

in which m and r independently of one another are 2 or 3, R₃₃ has one of the meanings of R₃ or is a group of the formulae I°d and I°e

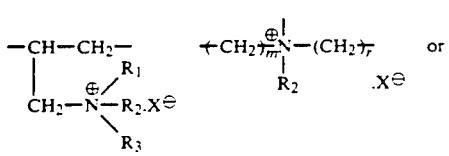

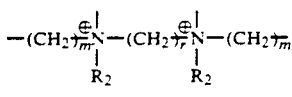

in which g, p, B, Y, A and U are as defined above, R₁, R₂ and R₃ independently of one another are C₁-C₈alkyl or C₁-C₈alkyl which is substituted by 1—COOR" group or by 1 to 3 OH groups, C₂-C₈hydroxyalkyl which is interrupted by one or more —O— groups, —(C₁-C₈)alkylene-COO⁻, —(C₁-C₈)alkylidene-COO⁻, —(C₂-C₈)alkylene-SO⁻₃ or —(C₂-C₈)alkylidene-SO⁻₃ each of which is substituted by one OH group, C₃-C₅alkenyl, C₅-C₇cycloalkyl, phenyl, tolyl, benzyl or glycidyl, or R₁, together with R₂ and if appropriate with R₃ and together with the N atom to which they are attached, form an N-heterocyclic radical which can contain 1-3 N atoms or one O atom as ring members, R" is hydrogen or C₁-C₄alkyl and X⁻ if not present in R₁, R₂, R₃ or R₃₃, is an organic or inorganic anion, subject to the conditions that A) in the event that U is a radical of the hydroxyphenylbenzotriazole type and n in the formula I° is 1, Y in the formula I°a has the meaning of Y₁, Y₁ being one of the following groups:

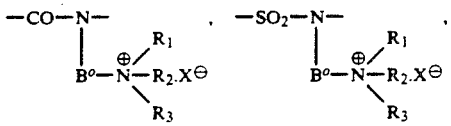

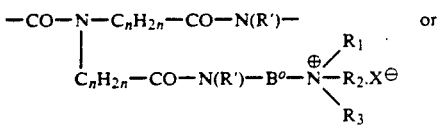

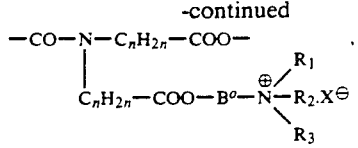

B) in the event that U is a radical of the hydroxybenzophenone type and n in the formula I° is 1 or 2, g is 0;

C) in the event that U is a cinnamic acid radical having 1 or 2 C≡N groups, n in the formula I° is 3 or 4; or D) in the event that U is a hydroxyphenyltriazine radical and, in the formula I°a, g is 1, A is alkylene and Y is a direct bond, B cannot be a direct bond or alkylene, or, if g is 1 and A is a direct bond, Y cannot be —CO—.

The possible examples of meanings for R₁, R₂, R₃, R', R", A, Y and B already given above under the formula I also apply here.

Preferred compounds are those of the formula I°, corresponding to a compound of the formula II° or III°

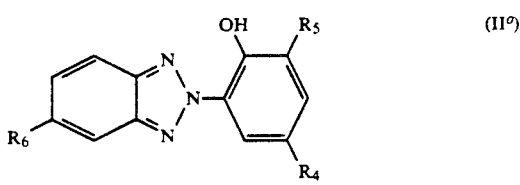

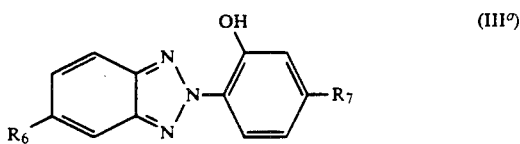

in which

R₄ is halogen, C₁-C₄alkoxy, C₁-C₈alkyl, C₅-C₆cycloalkyl, phenyl, phenyl-C₁-C₄alkyl or a group of the formula I°a, R₅ and R₆ independently of one another are hydrogen or have one of the meanings of R₄, and R₇ is OH, C₁-C₈alkoxy which can be substituted by 1 to 3 OH groups or 1 to 2 —COOH groups, C₁-C₈alkanoyloxy, a group of the formula I°a in which g is 1, or glycidyloxy, subject to the condition that at least one of R₄, R₅ and R₆ in the formula II° and at least one of R₆ and R₇ in the formula III° is a group of the formula I°a.

Amongst these, compounds which are particularly preferred are those of the formula I° in which R₄ is halogen, C₁-C₅alkyl, cyclohexyl or a group of the formula I°a, R₅ is hydrogen or has one of the meanings of R₄, R₆ is hydrogen, halogen or a group of the formula I°a, and R₇ is OH, C₁-C₄alkoxy which is unsubstituted or substituted by 1 to 3 OH groups or 1 to 2 COOH groups, glycidyloxy, C₂-C₃alkanoyloxy or a group of the formula I°a in which g is 1, particularly those in which, in the formula II°, R⁴ is C₁-C₄alkyl or a group of the formula I°f

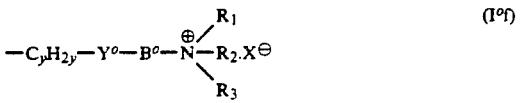

$R_5$ is hydrogen, $C_1-C_4$alkyl or a group $I^of$, and $R_6$ is hydrogen, Cl or a group $I^of$ in which y is 0, subject to the condition that at least one of $R_4$, $R_5$ and $R_6$ is a group $I^of$.

Compounds of interest are also those of the formula $I^o$, corresponding to a compound of the formula $V^o$

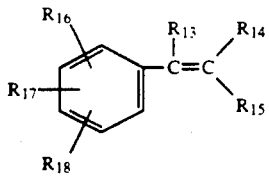

(V$^o$)

in which $R_{13}$ is hydrogen, $C_1-C_8$alkyl, $C_3-C_8$alkenyl, phenyl-$C_1-C_4$alkyl or a group of the formula

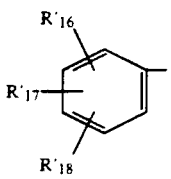

$R_{14}$ and $R_{15}$ independently of one another are —C≡N —CO—$C_1-C_4$alkyl, —COO—$R_{19}$ or —CO—$NR_{20}R_{21}$, $R_{16}$, $R_{17}$, $R_{18}$, $R'_{16}$, $R'_{17}$ and $R'_{18}$ independently of one another are hydrogen, $C_1-C_4$alkyl, phenyl, glycidyl, OH, halogen, $C_1-C_4$alkoxy which is unsubstituted or substituted by 1 to 3 OH groups, phenoxy, benzyloxy or a group of the formula $I^oa$ and $R_{19}$, $R_{20}$ and $R_{21}$ independently of one another are hydrogen, $C_1-C_4$alkyl which is unsubstituted or substituted by 1 to 3 OH groups, $C_5-C_7$cycloalkyl, phenyl, benzyl, tolyl, glycidyl or a group of the formula $I^og$ $$-B^o-\overset{\oplus}{\underset{R_3}{N}}\overset{R_1}{\underset{R_2}{}}\cdot X^{\ominus}$$ (I$^o$g)

in which $B^o$, $R_1$, $R_2$ and $R_3$ are as defined above, subject to the condition that at least one of $R_{16}$, $R_{17}$, $R_{18}$, $R'_{16}$, $R'_{17}$ or $R'_{18}$ is a group of the formula $I^oa$ and at least one of $R_{19}$, $R_{20}$ or $R_{21}$ is a group of the formula $I^og$ and, if $R_{14}$ and/or $R_{15}$ are C≡N, at least 3 groups of the formula $I^oa$ and/or $I^og$ are present.

Of these, compounds of particular interest are those which correspond to a compound of the formula $V^oa$

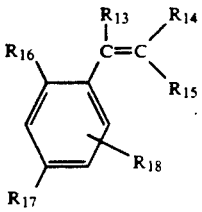

(V$^o$a)

in which $R^{13}$ is hydrogen, $C_1-C_4$ alkyl or a group

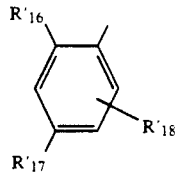

and $R_{14}$, $R_{15}$, $R_{16}$, $R_{17}$, $R_{18}$, $R'_{16}$, $R'_{17}$ and $R'_{18}$ are as defined above.

Compounds which are also of interest are those of the formula $I^o$, corresponding to a compound of the formula $VI^o$

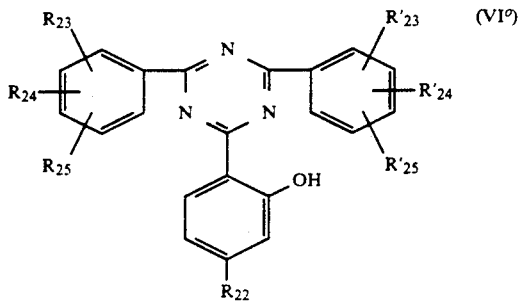

(VI$^o$)

in which $R_{22}$ is a group of the formula $I^oa$ in which g=1 and $R_{23}$, $R_{24}$, $R_{25}$, $R'_{23}$, $R'_{24}$ and $R'_{25}$ are hydrogen, OH, halogen, $C_1-C_4$alkoxy, $C_1-C_4$alkyl, phenyl or a group of the formula $I^oa$ in which g is 1, subject to the condition that, if g is 1, A is alkylene and Y is a direct bond in the formula $I^oa$, B is not a direct bond or alkylene, or, if g is 1 and A is a direct bond, Y cannot be —CO—.

Of these, compounds of particular interest are those which correspond to a compound of the formula $VI^oa$

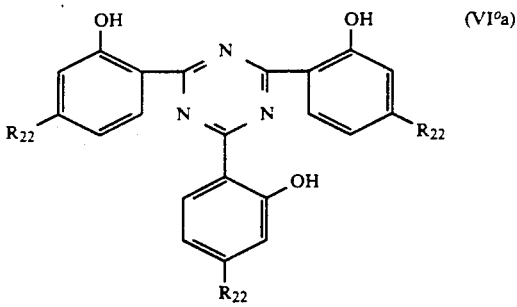

(VI$^o$a)

and $R_{22}$ is a group of the formula $I^oa$ in which g=1.

Compounds of the formula $I^o$ in which $X^{\ominus}$ in the formula $I^oa$ is halogen$^{\ominus}$, $C_1-C_4$alkyl-COO$^{\ominus}$, $C_1-C_4$alkyl-OSO$^{\ominus}_3$ or $R^o$—SO$^{\ominus}_3$ in which $R^o$ is methyl, tolyl or —CF$_3$, are also preferred.

The novel compounds of the formula $I^o$ can, as already described, be prepared by methods known per se.

The novel compounds of the formula $I^o$ can be used as stabilizers for organic materials in particular against damage caused thereto by light, oxygen and heat. The materials to be stabilized can, for example, be oils, fats, waxes, cosmetics, dyes or polymers. By virtue of their structure, they are advantageous for cathodic, electrophoretic coating and in paints and protective coatings based on water.

The novel compounds of the formula I° are preferably used as stabilizers for recording materials or inks for ink jet printing.

The following are examples of polymers which can advantageously be stabilized with the compounds, according to the invention, of the formula I:

1. Polymers of monoolefins and diolefins, for example polypropylene, polyisobutylene, polybut-1-ene, polymethylpent-1-ene, polyisoprene or polybutadiene, and polymers of cycloolefins, for example cyclopentene or norbornene; and also polyethylene (which can, if desired, be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene or of polypropylene with polyethylene (for example PP/HDPE or PP/LDPE) and mixtures of different types of polyethylene (for example LDPE/HDPE).

3. Copolymers of monoolefins and diolefins with one another or with other vinyl monomers, for example ethylene/propylene copolymers, linear, low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1, for example polypropylene-ethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (for example $C_5$–$C_9$), including hydrogenated modifications thereof (for example tackifying resins).

4. Polystyrene, poly-(p-methylstyrene) and poly-(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride or styrene/acrylonitrile/methyl acrylate; mixtures of high impact resistance formed from styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene or α-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene, styrene and maleimide or polybutathiene, styrene and alkyl acrylates or alkyl methacrylates on polybutadiene, styrene and acrylonitrile on ethylene/propylene/diene/terpolymers, styrene and acrylonitrile on polyalkyl acrylate or polyalkyl methacrylates, styrene and acrylonitrile on acrylate/butadiene copolymers and mixtures thereof with the copolymers mentioned under 5, such as are known, for example, as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers, in particular polymers formed from halogen-containing vinyl compounds, for example polyvinyl chloride, polyvinylidene chloride, polyvinyl fluoride or polyvinylidene fluoride; and copolymers thereof, such as vinyl chloride/vinylidene chloride, vinyl chloride/vinyl acetate or vinylidene chloride/vinyl acetate.

8. Polymers derived from α,β-unsaturated acids and derivatives thereof, such as polyacrylates and polymethacrylates, polyacrylamides and polyacrylonitriles.

9. Copolymers of the monomers mentioned under 8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers derived from unsaturated alcohols and amines or acyl derivatives or acetals thereof, such as polyvinyl alcohol, polyvinyl acetate, stearate, benzoate or maleate, polyvinylbutyral, polyallyl phthalate or polyallylmelamine; and copolymers thereof with olefins mentioned in item 1.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene, and also polyoxymethylenes containing comonomers, for example ethylene oxide, and polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters and polybutadienes having terminal hydroxyl groups on the one hand and from aliphatic or aromatic polyisocyanates on the other hand, and also precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12 or 4/6, polyamide 11, polyamide 12 and aromatic polyamides formed from m-xylene, diamine and adipic acid; and polyamides prepared from hexamethylenediamine and isophthalic and/or terephthalic acid and, if appropriate, an elastomer as modifier, for example poly-2,4,4-trimethylhexamethyleneterephthalamide or poly-m-phenyleneisophthalamide. Block copolymers of the polyamides mentioned above with polyolefins, olefin copolymers, ionomers or chemically attached or grafted elastomers; or with polyethers, for example polyethylene glycol, polypropylene glycol or polytetramethylene glycol. Also polyamides or copolyamides modified with EPDM or ABS; and polyamides which have been condensed during processing ("RIM polyamide systems").

16. Polyureas, polyimides, polyamide-imides and polybenzimidazoles.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates and block polyether-esters derived from polyethers having hydroxyl end groups; and also polyesters modified with polycarbonates or MBS.

18. Polycarbonates and polyester carbonates.

19. Polysulfones, polyether-sulfones and polyether ketones.

20. Crosslinked polymers derived from aldehydes on the one hand and phenols, urea or melamine on the other hand, such as phenol/formaldehyde, urea/formaldehyde and melamine/formaldehyde resins.

21. Drying and non-drying alkyd resins.

22. Unsaturated polyester resins derived from copolyesters of saturated and unsaturated dicarboxylic acids with polyhydric alcohols, and also vinyl compounds as crosslinking agents, and also halogen-containing modifications thereof of low flammability.

23. Crosslinkable acrylic resins derived from substituted acrylic acid esters, for example from epoxyacrylates, urethane acrylates or polyester acrylates.

24. Alkyd resins, polyester resins and acrylate resins crosslinked with melamine resins, urea resins, polyisocyanates or epoxy resins.

25. Crosslinked epoxy resins derived from polyepoxides, for example from bis-glycidyl ethers or cycloaliphatic diepoxides.

26. Natural polymers, such as cellulose, natural rubber, gelatine and their polymer-homologously chemically modified derivatives, such as cellulose acetates, propionates and butyrates or the cellulose ethers, such as methylcellulose; and also colophony resins and derivatives.

27. Mixtures (polyblends) of the abovementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic PUR, POM/acrylate, POM/MBS, PPO/HIPS, PPO/PA 6.6 and copolymers, PA/HDPE, PA/PP and PA/PPO.

28. Natural and synthetic organic substances which are pure monomeric compounds or mixtures of such, for example mineral oils, animal or vegetable fats, oils and waxes, or oils, waxes and fats based on synthetic esters (for example phthalates, adipates, phosphates or trimellitates), and mixtures of synthetic esters with mineral oils in any desired weight ratios, such as are used, for example, as spin preparations, and aqueous emulsions thereof.

29. Aqueous emulsions of natural or synthetic rubbers, for example natural rubber latex or latices of carboxylated styrene/butadiene copolymers.

The stabilizers according to the invention are advantageously added to the polymers in a concentration of 0.01–10% by weight, calculated on the material to be stabilized. It is preferable to incorporate into the material to be stabilized 0.05 to 5.0% by weight, particularly preferably 0.1 to 2.0% by weight, of the compounds of the formula I, calculated on the former.

The incorporation can, for example, be effected by mixing in the stabilizers according to the invention and, if appropriate, further additives by the methods customary in the industry, before or during shaping, or by applying the dissolved or dispersed compounds to the polymer, if appropriate with subsequent evaporation of the solvent. The stabilizers according to the invention can also be added to the plastics to be stabilized in the form of a master-batch containing the stabilizer in a concentration of, for example, 2.5 to 25% by weight.

The compounds of the formula $I^o$ can also be added before or during the polymerization or crosslinking reaction. Stabilized polymers are thus obtained without further treatment.

The materials stabilized in this way can be used in a very wide variety of forms, for example as films, fibres, tapes, moulding materials or profiles or as binders for paints, adhesives or cements.

The use of the compounds according to the invention in paints of all types is particularly preferred. These can be pigmented or unpigmented paints or metallic effect paints. They can contain an organic solvent or can be solvent-free or can be aqueous paints. The use of aqueous paints, such as are used, for example, for electrophoretic coatings or for wood painting is particularly important.

The paints can contain, as the binder, at least one of the polymers listed above. The following are examples of paints having special binders:

1. paints based on cold-crosslinkable or hot-crosslinkable alkyd, acrylate, polyester, epoxy or melamine resins or mixtures of such resins, if desired with the addition of an acid curing catalyst;

2. two-component polyurethane paints based on acrylate, polyester or polyether resins containing hydroxyl groups, and aliphatic or aromatic polyisocyanates;

3. one-component polyurethane paints based on masked polyisocyanates which are unmasked during stoving;

4. two-component paints based on (poly)ketimines and aliphatic or aromatic polyisocyanates;

5. two-component paints based on (poly)ketimines and an unsaturated acrylate resin or a poyacetoacetate resin or a methyl methacrylamidoglycollate methyl ester;

6. two-component paints based on polyacrylates and polyepoxides containing carboxyl or amino groups;

7. two-component paints based on acrylate resins containing anhydride groups, and a polyhydroxy or polyamino component;

8. two-component paints based on (poly)oxazolidines and acrylate resins containing anhydride groups or unsaturated acrylate resins or aliphatic or aromatic polyisocyanates;

9. two-component paints based on unsaturated polyacrylates and polymalonates;

10. thermoplastic polyacrylate paints based on thermoplastic acrylate resins or extraneously-crosslinking acrylate resins in combination with etherified melamine resins; and 11. paint systems based on acrylate resins modified with siloxanes.

The paints can also be radiation-curable paints. In this case the binder consists of monomeric or oligomeric compounds which contain ethylenic double bonds and pass over into a crosslinked, high-molecular form as the result of irradiation with actinic light or electron beams. In most cases this involves a mixture of such compounds.

The paints can be applied as one-coat or two-coat paints, it being preferable to add the stabilizers according to the invention to the unpigmented top layer. In addition to the stabilizers according to the invention, it is also possible for such paints to contain the additives enumerated in paragraphs 1 to 10 below. In particular, combinations of these stabilizers with the sterically hindered amines mentioned under 2.7 display good stabilizing effects.

The paints can be applied to the substrates (metal, plastic, wood etc.) by the customary processes, for example by brushing, spraying, pouring, dipping or electrophoresis.

In practice, the stabilizers according to the invention can be employed together with other stabilizers.

The following may be mentioned as examples of further additives with which the stabilizers used in accordance with the invention can be employed jointly:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol and 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone and 2,6-diphenyl-4-octadecyloxyphenol.

1.3. Hydroxylated thiodiphenyl ethers, for example 2,2'-thiobis-(6-tert-butyl-4-methylphenol), 2,2'-thiobis-(4-octylphenol), 4,4'-thiobis-(6-tert-butyl-3-methylphenol), 4,4'-thiobis-(6-tert-butyl-2-methylphenol).

1.4. Alkylidene bisphenols, for example 2,2'-methylenebis-(6-tert-butyl-4-methylphenol), 2,2'-methylenebis-(6-tert-butyl-4-ethylphenol), 2,2'-methylenebis-[4-methyl-6-(α-methylcyclohexyl)-phenol], 2,2'-methylenebis-(4-methyl-6-cyclohexylphenol), 2,2'-methylenebis-(6-nonyl-4-methylphenol), 2,2'-methylenebis-(4,6-di-tert-butylphenol), 2,2'-ethylidenebis-(4,6-di-tert-butylphenol), 2,2'-ethylidenebis-(6-tert-butyl-4-isobutylphenol), 2,2'-methylenebis-[6-(α-methylbenzyl)-4-nonylphenol], 2,2'-methylenebis-[6-(α,α-dimethylbenzyl)-4-nonylphenol], 4,4'-methylenebis-(2,6-di-tert-butylphenol), 4,4'-methylenebis-(6-tert-butyl-2-methylphenol), 1,1-bis-(5-tert-butyl-4-hydroxy-2-methylphenyl)-butane, 2,6-bis-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate, bis-(3-tert-butyl-4-hydroxy-5-methylphenyl)-dicyclopentadiene and bis-[2-(3'-tert-butyl-2'-hydroxy-5'-methylbenzyl)-6-tert-butyl-4-methylphenyl] terephthalate.

1.5. Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl) sulfide, isooctyl 3,5-di-tert-butyl-4-hydroxybenzylmercaptoacetate, bis-(4-tert-butyl-3-hydroxy-2,6-dimethylbenzyl)-dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate, the Ca salt of monoethyl 3,5-di-tert-butyl-4-hydroxybenzylphosphonate and 1,3,5-tris-(3,5-dicyclohexyl-4-hydroxybenzyl) isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine and octyl N-(3,5-di-tert-butyl-4-hydroxyphenyl)-carbamate.

1.7. Esters of (β-(3,5-di-tert-butyl-4-hydroxyphenyl)-propionic acid, with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate and N,N'-bis-(hydroxyethyl)oxamide.

1.8. Esters of β-(5-tert-butyl-4-hydroxy-3-methylphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate and N,N'-bis-(hydroxyethyl)oxamide.

1.9. Esters of β-(3,5-dicyclohexyl-4-hydroxyphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate and N,N'-bis-(hydroxyethyl)oxamide.

1.10. Amides of β-(3,5-di-tert-butyl-4-hydroxyphenyl)-propionic acid, for example, N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

2. Other UV Absorbers and Light Stabilizers 2.1. 2-(2'-hydroxyphenyl)-benzotriazoles, for example the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, 3',5'-di-tert-amyl-, 3',5'-bis-(α,α-dimethylbenzyl)- derivative. Also mixtures of polyethylene glycol 300 β-[3-(2H-benzotriazol-2-yl)-4-hydroxy-5-t-butylphenyl]propionate and polyethylene glycol 300 bis-{β-[3-(2H-benzotriazol-2-yl)-4-hydroxy-5-t-butylphenyl]-propionate}.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy- derivative.

2.3. Esters of substituted or unsubstituted benzoic acids, for example 4-tert-butylphenyl salicylate, phenyl salicylate, octylphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-β-cyanovinyl)-2-methylindoline.

2.5. Nickel compounds, for example nickel complexes of 2,2'-thiobis-[4-(1,1,3,3-tetramethylbutyl)-phenol], such as the 1:1-complex or the 1:2 complex, if appropriate with additional ligands, such as n-butylamine, triethanolamine or N-cyclohexyldiethanolamine, nickel dibutyldithiocarbamate, nickel salts of monoalkyl 4- hydroxy-3,5-di-tert-butylbenzylphosphonates, such as the methyl or ethyl ester, nickel complexes of ketoximes, such as 2-hydroxy-4-methylphenyl undecyl ketoxime, or nickel complexes of 1-phenyl-4-lauroyl-5-hydroxypyrazole, if appropriate with additional ligands.

2.6. 2-(2-Hydroxyphenyl)-1,3,5-triazines, for example 2,4,6-tris-(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis-(2,4-dimethylphenyl)-1,3,5-triazine, 2,4-bis-(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine or 2-(2-hydroxy-4-dodecyloxyphenyl)-4,6-bis-(2,4-dimethylphenyl)-1,3,5-triazine.

2.7. Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product formed from 1-hydroxyethyl-2,2,6,6-tetramethyl-4-hydroxypiperidine and succinic acid, the condensation product formed from N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetraoate or 1,1'-(1,2-ethanediyl)-bis-(3,3,5,5-tetramethyl-piperazinone).

2.8. Oxamides, for example 4,4'-di-octyloxyoxanilide, 2,2'-di-octyloxy-5,5'-di-tert-butyloxanilide, 2,2'-didodecyloxy-5,5'-di-tert-butyloxanilide, 2-ethoxy-2'-ethyloxanilide, N,N'-bis-(3-dimethylaminopropyl)-oxamide, 2-ethoxy-5-tert-butyl-2'-ethyloxanilide and a mixture thereof with 2-ethoxy-2'-ethyl-5,4'-di-tert-butyloxanilide or mixtures of o-methoxy- and p-methoxy-disubstituted oxanilides and of o-ethoxy- and p-ethoxy-disubstituted oxanilides.

2.9.1. Cationic UV absorbers containing at least one quaternary ammonium group for example those described in JP-A 61-19,278, 61-192,778 and 61-192,780 and FR-A 1,464,919.

2.9.2. Anionic UV absorbers and salts thereof, such as are described, for example, in JP-A 54-085,804, 54-068,303, 62-106,971, 63-046,277, 59-027,972 and 59-169,883.

3. Metal deactivators, for example N,N'-diphenyloxamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole and bis-(benzylidene)-oxalic acid dihydrazide.

4. Phosphites and phosphonites, for example triphenyl phosphite, diphenyl alkyl phosphites, phenyl dialkyl phosphites, tris-(nonylphenyl)phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, tristearyl sorbitol triphosphite, tetrakis-(2,4-di-tert-butylphenyl) 4,4'-biphenylene diphosphonite and 3,9-bis-(2,4-di-tert-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl esters, mercaptobenzamidazole, the zinc salt of 2-mercaptobenzimidazole, zinc dibutyldithiocarbamate, dioctadecyl disulfide and pentaerythrityl tetrakis-(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example Ca stearate, Zn stearate, Mg stearate, Na ricinoleate and K palmitate, antimony pyrocatecholate or tin pyrocatecholate.

8. Nucleating agents, for example 4-tert-butylbenzoic acid, adipic acid or diphenylacetic acid.

9. Fillers and reinforcing agents, for example calcium carbonate, silicates, glass fibres, asbestos, talc, kaolin, mica, barium sulfate, metal oxides and hydroxides, carbon black or graphite.

10. Other additives, for example plasticizers, lubricants, emulsifiers, pigments, fluorescent brighteners, fire-retarding agents, antistatic agents or blowing agents.

The following examples illustrate the invention further. Percentages are by weight, unless stated otherwise.

PREPARATION EXAMPLES

EXAMPLE 1 a) Preparation of 1,3-bis-(N,N-dimethylamino)-2-propyl 3-[3-(2-benzotriazolyl)-4-hydroxy-5-t-butylphenyl]-propionate

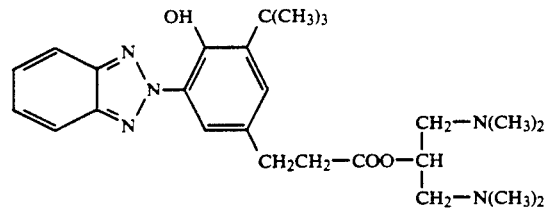

100 g of 3-[3-(2-benzotriazolyl)-4-hydroxy-5-t-butylphenyl]-propionic acid are suspended in 600 ml of toluene. 10 ml of dimethylformamide (DMF) are added, and the mixture is heated to 70° C. 70.1 g of thionyl chloride are then added dropwise to the mixture. Evolution of HCl and $SO_2$ is observed in the course of this. The solution is stirred for 4 hours at 80° C. Finally, the excess thionyl chloride is removed by distillation. 50.9 g of 1,3-bis-(N,N-dimethylamino)-propan-2-ol are added dropwise to the solution at 80° C., HCl being evolved.

The reaction mixture is stirred for 8 hours at 80° C. and is then cooled to 10° C. The hydrochloride precipitate is filtered off, extracted by washing with ether and then dissolved in 1 l of water and neutralized with 10 ml of conc. $NH_3$ ($NH_3$ containing 25% of $H_2O$). The product is extracted with methylene chloride.

The organic phase, containing the crude product, is washed with aqueous NaCl solution, dried over $MgSO_4$ and concentrated. The residue is recrystallized from a petroleum ether/ethyl acetate mixture.

54.4 g of 1,3-bis-(N,N-dimethylamino)-2-propyl 3-[3-(2-benzotriazolyl)-4-hydroxy-5-t-butylphenyl]-propionate are obtained in the form of white crystals (melting point 79°–80° C.).

b) Preparation of
1,3-bis-(N,N,N-trimethylammonium)-2-propyl
3-[3-(2-benzotriazolyl)-4-hydroxy-5-t-butylphenyl]-propionate di-monomethyl sulfate

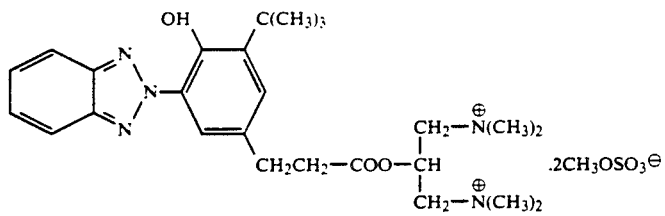

20 g of 1,3-bis-(N,N-dimethylamino)-2-propyl 3-[3-(2-benzotriazolyl)-4-hydroxy-5-t-butylphenyl]-propionate are dissolved in 200 ml of acetone, and 21.6 g of dimethyl sulfate are added dropwise. An exothermic reaction takes place and a white precipitate is formed. The reaction mixture is heated at reflux temperature for 1 hour. The precipitate is then filtered off and washed with acetone. Recrystallization from methanol gives 17.4 g of 1,3-bis-(N,N,N-trimethylammonium)-2-propyl 3-[3-(2-benzotriazolyl)-4-hydroxy-5-t-butylphenyl]-propionate di-monomethyl sulfate in the form of white crystals (melting point 196°–203° C.).

EXAMPLE 2

1,3-bis-(N,N,N-trimethylammonium)-2-propyl
3-[3-(2-benzotriazolyl)-4-hydroxy-5-t-butylphenyl]-propionate dichloride

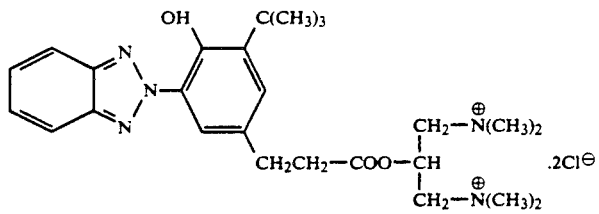

20 g of 1,3-bis-(N,N-dimethylamino)-2-propyl-3-[3-(2-benzotriazolyl)-4-hydroxy-5-t-butylphenyl]-propionate are dissolved in 360 ml of acetone/methylene chloride (4:1 parts by volume). Methyl chloride is passed through the solution for 30 minutes, and the flask is then closed and allowed to stand overnight. The resulting precipitate is filtered off, washed with approx. 100 ml of petroleum ether and dried. Recrystallization from a methylene chloride/petroleum ether mixture gives 24.0 g of 1,3-bis-(N,N,N-trimethylammonium)-2-propyl 3-[3-(2-benzotriazolyl)-4-hydroxy-5-t-butylphenyl]-propionate dichloride in the form of white crystals (melting point 105°–110°, combined with decomposition).

EXAMPLE 3 a) Preparation of
3,5-bis-{5'-[2''-(N,N-dimethylamino)-ethoxycarbonyl]-2'-methylpent-2'-yl}-2-hydroxyphenylbenzotriazole

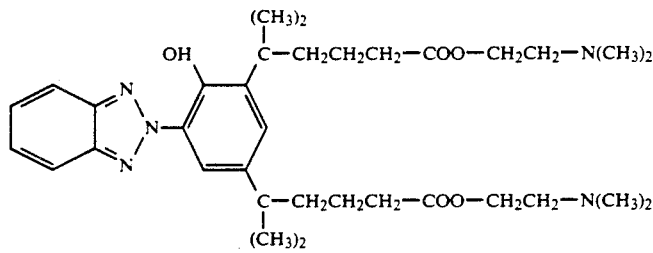

The procedure is as in Example 1a), but using 23.4 g o (0.05 mol) of the corresponding dicarboxylic acid. 33.5 g (0.049 mol) of the bis-hydrochloride are obtained (98% of theory; melting point 195°–198° C.). The product is then neutralized and purified by chromatography (Alox Type E using acetoacetic ester/petroleum ether in a 1:3 ratio by volume). 23.5 g (0.039 mol) of the diamine are obtained in the form of a slightly yellowish oil (80% of theory).

| Analysis | % C | % H | % N |
|---|---|---|---|
| Calculated: | 66.97 | 8.43 | 11.48 |
| Found: | 66.90 | 8.51 | 11.39 | b) Preparation of 3,5-bis-{5'-[2"-(N,N,N-trimethylammonium)-ethoxycarbonyl]-2'-methylpent-2'-yl}-2-hydroxyphenylbenzotriazole bis-monomethyl sulfate

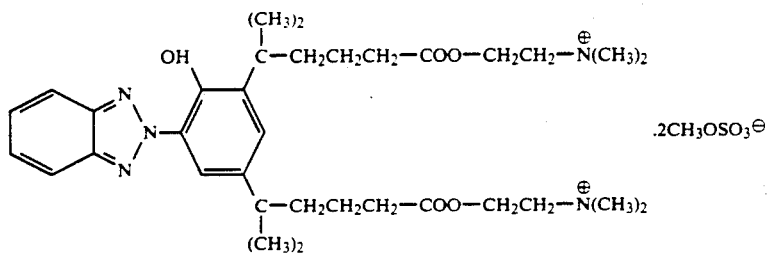

The procedure is analogous to Example 1b), employing 3.0 g of the product from Example 1a).

3.5 g of the desired substance are obtained in the form of white crystals (melting point 50°-65° C.).

EXAMPLE 4

Preparation of 1,3-bis-(N,N,N-trimethylammonio)-2-propyl 3-[3-(5-chloro-2-benzotriazolyl)-4-hydroxy-5-t-butylphenyl]-propionate diiodide

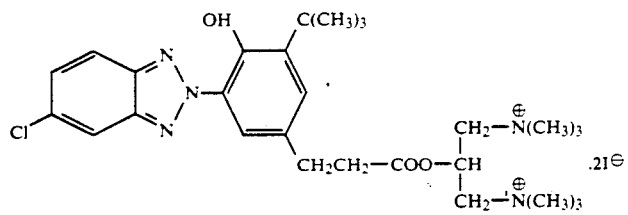

The procedure is analogous to Examples 1 and 2, but using 100 g of the corresponding carboxylic acid and methyl iodide instead of methyl chloride. 43 g of the product are obtained in the form of slightly yellowish crystals (melting point 180°-187° C.).

EXAMPLE 5

Preparation of {3-([4-(2-benzotriazolyl)-3-hydroxyphenoxy]-2-hydroxy-1-propyl}-N,N,N-trimethylammonium chloride

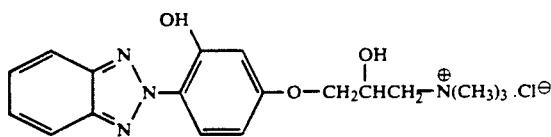

11.4 g (0.05 mol) of 2-(2,4-dihydroxyphenyl)-benzotriazole, together with 7.75 g (0.051 mol) of glycidyltrimethylammonium chloride, are heated in 100 ml of acetonitrile for 24 hours at 50°-60° C.

The precipitate is filtered off and heated to reflux temperature in 20 ml of acetonitrile. Cooling and filtration gives 3.7 g of a pale yellow solid (melting point 225°-228° C.).

EXAMPLE 6

Preparation of 1,3-bis-(N,N,N-trimethylammonio)-2-propyl 2-cyano-3,3-diphenylacrylate bis-monomethyl sulfate

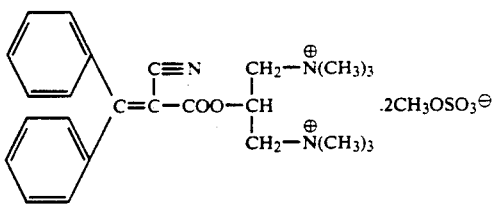

The procedure is analogous to Example 1, but using 12.5 g of 2-cyano-3,3-diphenylacrylic acid. 7.1 g of the product are obtained in the form of white crystals (melting point 189°-191° C.).

EXAMPLE 7

Preparation of 2-N,N-dimethylaminoethyl 2-[3,5-di-tert-butyl-2-hydroxyphenyl]-5-benzotriazolecarboxylate

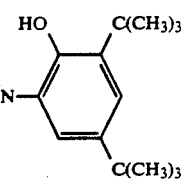

The procedure is analogous to Example 1, but using 36.7 g of 2-[3,5-di-tert-butyl-2-hydroxyphenyl]-5-benzotriazolecarboxylic acid and 9.8 g of 2-N,N-dimethylaminoethanol. 37.0 g (89%) of theory) of the product are obtained in the form of slightly yellowish crystals (melting point 127°-129° C.).

EXAMPLE 8

Preparation of 2-[3,5-di-tert-butyl-2-hydroxyphenyl]-5-[2C-N-2-hydroxyethyl-N,N-dimethylammonio)-ethoxycarbonyl]-benzotriazole bromide

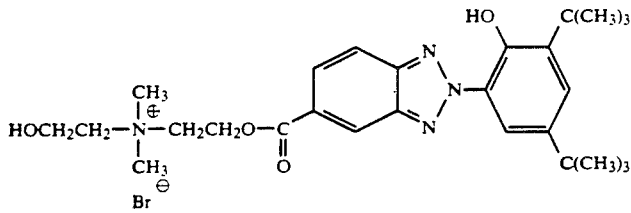

17.5 g of 2-N,N-dimethylaminoethyl 2-[3,5-di-tert-butyl-2-hydroxyphenyl]-5-benzotriazolecarboxylate are dissolved in 70 ml of toluene. 25 g of 2-bromoethanol are added and the solution is boiled under reflux for 15 hours. It is then allowed to cool, in the course of which the product is precipitated. It is filtered off, washed with diethylether and dried in vacuo. 17.0 g (75% of theory) of the product are obtained in the form of yellowish crystals (melting point 222°-224° C.).

EXAMPLE 9

Preparation of [N,N-bis-2-chloroethyl]-3-[3-(2-benzotriazolyl)-4-hydroxy-5-t-butylphenyl]-propionamide

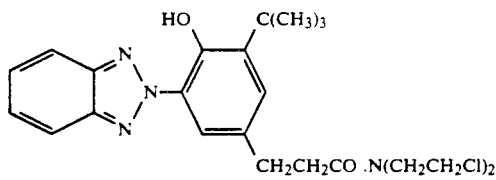

The procedure is analogous to Example 1, but using 33.9 g of 3-[3-(2-benzotriazolyl)-4-hydroxy-5-t-butylphenyl]-propionic acid and 19.6 g of bis-(2-chloroethyl)-amine. The product is purified by chromatography (Alox Type E, 1:4 v/v ethyl acetate/petroleum ether). 5 g of the product are obtained in the form of white crystals (melting point 90°-93° C.).

EXAMPLE 10

Preparation of [N,N-bis-[(N,N,N-trimethylammonium)-2-ethyl]-3-[3-(2-benzotriazolyl)-4-hydroxy-5-t-butylphenyl]-propionamide dichloride

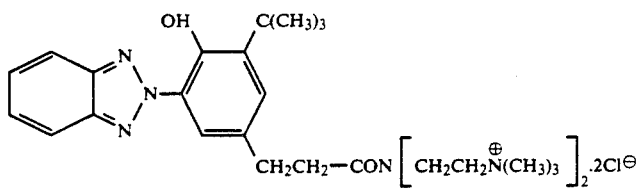

1.16 g of [N,N-bis-2-chloroethyl]-3-[3-(2-benzotriazolyl)-4-hydroxy-5-t-butylphenyl]propionamide are dissolved in 10 ml of toluene. 4.8 ml of a solution of trimethylamine (4.2M) in ethanol and 0.1 ml of DMF are added, and the mixture is heated in a bomb tube for 24 hours at 100° C. It is then allowed to cool, in the course of which the product is precipitated. After washing with diethyl ether and drying in vacuo, 1.3 g (84% of theory) of the dichloride are obtained in the form of white, hygroscopic crystals (melting point 110°-120° C.).

USE EXAMPLE 1

Preparation of Ink Jet Printing Coatings

A. Coating Without Stabilizer 16.4 g of a 10% aqueous solution of polyvinyl alcohol are mixed with 0.03 g of di-t-octylphenol-polyethylene oxide wetting agent and 0.3 g of Polyfix ® 601 (Showa High Polymer Co.) mordant, and the mixture is made up to 27.0 g with water. 2.0 g of silica (Syloid ® Type 244, Grace & Co.) are stirred into the solution and dispersed ultrasonically. The pH of the dispersion is adjusted to 7.0 with 2N NaOH.

B. Coating Containing a Stabilizer

A dispersion is prepared analogously to the description under A, but the Polyfix ® 601 mordant is replaced by 0.6 g of the compound from Example 1b)

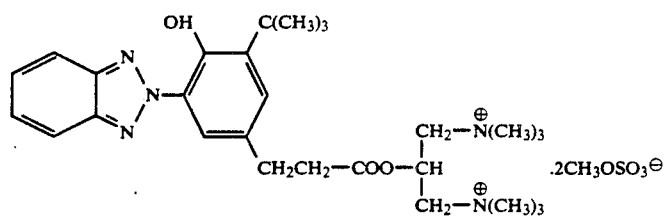

The aqueous phase amounts to 32.4 g in total.

The resulting pouring mixtures A and B are applied to photographic paper in a thickness of 50 μm by means of a wire spiral.

The coatings obtained after drying have a dry weight of 7 g/m², B containing 1 g/m² of the stabilizer.

The recording materials prepared in this manner are each used to print with a purple-red ink in a "think-jet" ink jet printing apparatus (Hewlett-Packard). The inks have the following composition:
5 parts of C.I. Acid Red 35 or C.I. Acid Red 249,
50 parts of diethylene glycol and
45 parts of water.

The inks are filtered through an ultrafilter having a pore width of 0.3 μm and are filled into the ink cartridge of the "think-jet" apparatus. Printed samples having a dot density of 192×96 dots per inch are produced.

The ink density (intensity) of the printed samples is then determined with a Densitometer (Macbeth TR 924), using a Status A filter.

Testing fastness to light

The fastness to light of the printed samples is tested by irradiating the samples in an Atlas Weatherometer using a xenon lamp of luminous intensity 81 klux behind a filter made of window glass 6 mm thick.

The ink density is measured again in order to determine the percentage loss in ink density.

The results are summarized in Table 1 below. Lower values mean higher fastness to light.

TABLE 1

| Sample | LOSS IN INK DENSITY (%) | |
|---|---|---|
| | Acid Red 35 5 kJ/cm²* | Acid Red 249 15 kJ/m²* |
| A (without stabilizer) | 86 | 84 |
| B (with stabilizer) | 38 | 48 |

*Quantity of radiation energy within the range from 300–800 nm found by measurement

Testing Fastness to Washing

The sample printed with coating B is washed in a drum developing apparatus (Jobo Autolab ATL-1). (This apparatus is usually employed for developing photographic materials). The printed sample is in each case washed 10 times in the drum developing apparatus for 30 seconds with water at 25° C. The drum speed here is the minimum, in order to avoid mechanical damage to the coating on the sample.

The sample is then dried and its ink density is measured in order to determine the percentage ink loss in the washing process. The results are summarized below.

TABLE 2

| Sample | LOSS IN INK DENSITY (%) | |
|---|---|---|
| | Acid Red 35 5 kJ/cm²* | Acid Red 249 15 kJ/m²* |
| B (with stabilizer) | 0 | 0 |

It can be seen from the results obtained that the recording materials according to the invention, which contain a compound of the formula I as stabilizer, have an outstanding fastness to light and are at the same time fast to washing.

Use Example 2

A solution (A) of the dye C.I. Acid Yellow 23, which has an extremely poor resistance to water in ink jet prints, is prepared as follows:
3 g of C.I. Acid Yellow 23,
30 g of diethylene glycol and
67 g of water.

A second solution (B) is prepared from:
3 g of the compound from Example 1b,
30 g of diethylene glycol and
67 g of water.

Inks for ink jet printing can be prepared by either adding solution A to solution B or conversely. Thus 3.1 g of solution A can be added with stirring to 10 g of solution B before cloudiness sets in. Similarly, 10 g of solution B can be added to 10 g of solution A without the formation of a precipitate.

The two solvent mixtures are filtered through a filter of pore width 0.3 μm and are used as ink for ink jet printing analogously to Use Example 1.

Two blank samples are also prepared. They consist of solution A and solution C in the same ratios as the inks made from solution A and solution B.

For this purpose, solution C is prepared as follows:
3 g of solution A,
30 g of diethylene glycol and
67 g of water.

The ink jet printing paper used is a paper having a 5 g/m² coating consisting of 2.24 g/m² of polyvinyl alcohol, 2.73 g/m² of silica and 0.03 g/m² of di-t-octylphenylpolyethylene oxide (8EO). This paper is printed as described in Use Example 1 with the inks, and its fastness to washing is tested. The results are summarized in Table 3. Low values mean higher fastness to washing.

TABLE 3

| Sample of composition | | | LOSS IN INK DENSITY (%) |
|---|---|---|---|
| Part A | Part B | Part C | Acid Yellow 23 |
| 10 | 10 | — | 92 |
| 10 | — | 10 | 96 |
| 3.1 | 10 | — | 84 |
| 3.1 | — | 10 | 90 |

This example shows that the compounds of the formula I can be put straight into the ink for ink jet printing and that these inks impart improved resistance to water to ink jet prints.

Use Example 3

Coating compositions for ink jet printing papers are prepared analogously to Use Example 1 from 16.4 g of a 10% polyvinyl alcohol solution (Riedel de Haen), 0.015 g of Invadin® JFC wetting agent (Ciba-Geigy), 0.52 g of a UV absorber according to the invention, 2.0 g of silica (Syloid® Type 244, W. R. Grace) and water to 33.2 g. The pH is adjusted to 7.0 with lithium hydroxide. The composition thus obtained is applied to polyethylene-coated paper by means of a 60 μm doctor blade curtain coating machine and is dried. The paper then has a coating of 8 g/m², of which 1 g/m² relates to the UV absorber.

As a comparison, sheets of paper having in each case 0.52 g of a 10% mordant solution instead of the 0.52 g of UV absorber are prepared. This corresponds to a mordant coating of approx. 0.1 g/m².

The mordants used are the products Polyfix 601 (Showa High Polymer Co.), Merquat 100 (Chemviron), Tinofix EW (Ciba-Geigy AG) and polyallylamine HCl (Nitto Boseki Col.), which are described, for example, in German Patent 3,640,359 and Japanese Patent 61-061,887.

These sheets of paper are printed as described in Use Example 1 with an ink consisting of 4 g of C.I. Acid Red 35 in a mixture of 48 g of water and 48 g of diethylene glycol (cf. Use Example 1). The fastness to light and the fastness to washing are then determined as in Use Example 1. The results are summarized in Table 3.

TABLE 3

| Sample | UV-absorber/ mordant | Loss in density (%) | |
|---|---|---|---|
| | | After Atlas irradiation of 10 kJ/cm² | In the fastness to washing test |
| 1 | Compound according to Preparation Example 1b | 46 | 0 |
| 2 | Compound according to Preparation Example 2 | 43 | 0 |
| 3 | Compound according to Preparation Example 8 | 38 | 0 |
| 4 | Compound according to Preparation Example 10 | 48 | 0 |
| 5 | none | 82 | 92 |
| 6 | Polyfix 601 | 81 | 88 |
| 7 | Polyallylamine HCl | 88 | 32 |
| 8 | Merquat 100 | 88 | 28 |
| 9 | Tinofix EW | 85 | 34 |

Use Example 4

It will be shown in this example that even minor amounts of UV absorbers according to the invention produce an improvement in fastness to light in ink jet printing paper.

Coating compositions are prepared containing in each case 14.9 g of a 10% solution of polyvinyl alcohol, 0.015 g of Invadin ® JFC wetting agent, 0.24 g of a UV absorber according to the invention, 0.27 g of polyfix 601 solution (Showa High Polymer Co.), 2.0 g of silica and water up to 30.5 g. The coating compositions are applied to a paper carrier. After drying, the papers thus obtained are printed with the ink jet printing ink containing the dye C.I. Acid Red 35 according to Use Example 3. The fastness to light of the printed samples is then tested as described in Use Example 1. The results are summarized in Table 4.

TABLE 4

| Sample | UV absorber | Loss in ink density (%) after 10 kJ/cm² |
|---|---|---|
| 1 | None | 78 |
| 2 | Compound according to Preparation Example 1a* | 62 |
| 3 | Compound according to Preparation Example 1b | 51 |
| 4 | Compound according to Preparation Example 2 | 50 |
| 5 | Compound according to Preparation Example 3b | 75 |
| 6 | Compound according to Preparation Example 6 | 72 |
| 7 | Compound according to Preparation Example 8 | 63 |
| 8 | Compound according to Preparation Example 10 | 59 |

*For reasons of solubility, the ink jet printing paper has to be coated with the coating composition at pH 5.0 (adjusted by means of H₂SO₄).

Use Example 5

An aqueous clear lacquer of the following composition is prepared

| | |
|---|---|
| Synthacryl ® VSW 6484 (50%) | 31.45 parts |
| Maprenal ® MF 915 (75%) | 12.52 parts |
| Maprenal ® MF 927 (70%) | 1.64 parts |
| Additol ® XW 329 | 0.04 part |
| Demineralized water | 20.00 parts |
| Synthacryl ® VSW 6483 (50%) | 22.49 parts |
| Demineralized water | 11.86 parts |

1.5% of stabilizer (relative to lacquer solids) are incorporated into the clear lacquer for 5 minutes at 3000 r.p.m. The spraying strength of the resulting lacquer is adjusted with demineralized water and it is sprayed onto a previously prepared substrate (coil coat metal sheet with filter and aqueous silver metallic base paint). The metal sheet is stoved for 10 minutes at 80° C. and then for 30 minutes at 140° C. The metal sheet thus obtained is tested after outdoor weathering in Florida.

The comparison used is a corresponding lacquer with no stabilizer, which is used to coat an identical metal sheet in the manner described above. The results are shown in Table 5.

TABLE 5

| Sample | UV absorber | % DOI*) ⊕ |
|---|---|---|
| 1 | — | 49⊕ |
| 2 | Compound**) | 85 |
| 3 | Compound according to Preparation Example 8 | 89 |

*)Distinctness of reflected image (ASTM E 430) after outdoor weathering for three months in Florida

**)(CH₃)₂NCH₂CH₂O—C(=O)— [benzotriazole with HO, C(CH₃)₃, C(CH₃)₃ substituents]  CH₃OSO₃⊖

What is claimed is:

1. A recording material containing, as the stabilizer, at least one compound of formula VI $$\text{(VI)}$$

[structure with R₂₃, R₂₄, R₂₅, R'₂₃, R'₂₄, R'₂₅, R₂₂, OH groups]

in which
R₂₂ is a group of formula Ia $$\text{(Ia)}$$

$$\mathrm{+O{\overline{)}_g}A-Y-B-N\begin{array}{c}R_1\\ -R_2 \cdot X^\ominus\\ R_{33}\end{array}}$$

in which
g is 1,
A is a direct bond, C₂-C₆alkylene, C₂-C₆alkylidene or a group of the formula Ib

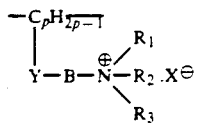 (Ib)

in which p is a number from 1 to 6, Y is a direct bond or one of the following groups:

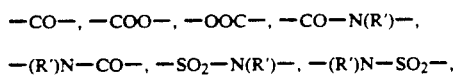

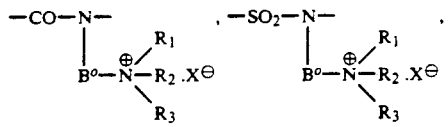

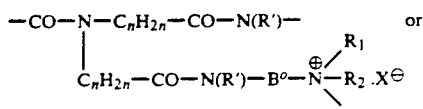

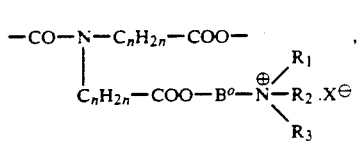

B is a direct bond or $C_2$-$C_6$alkylene or $C_2$-$C_6$alkylidene which is unsubstituted or substituted by OH and which can be interrupted by one —O— or by one or two —N(R')$_2$—, or is a group of the formulae Ic or IC

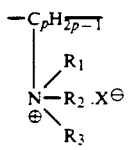 (Ic)

or

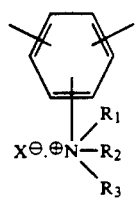 (IC)

or the group

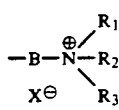

is a saturated or unsaturated mononuclear to trinuclear N-heterocyclic radical containing 1–4 N atoms as ring members, at least one of which is quaternized, subject to the conditions that a) in the event that g=1, A, Y and B are not at the same time a direct bond;

b) in the event that g—=1 and A=a direct bond, Y is —CO— or a direct bond; and c) in the event that B=a direct bond, Y is also a direct bond;

R' is hydrogen, $C_1$-$C_4$alkyl or $C_2$-$C_3$hydroxyalkyl, B$^o$ is —(CH$_2$) or one of the following groups:

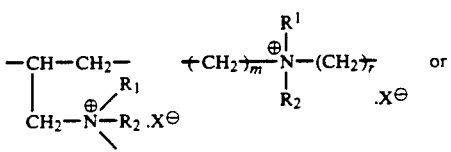

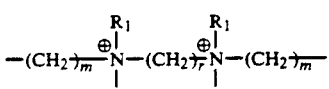

in which m and r independently of one another are 2 or 3, $R_{33}$ has one of the meanings of $R_3$ or is a group of the formulae Id and Ie

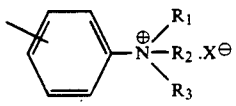 (Id)

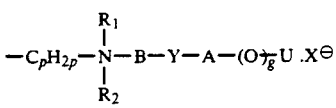 (Ie)

in which g, p, B, Y and A are as defined above,

U is a radical of a UV absorber of the hydroxyphenyltriazine type, $R_1$, $R_2$ and $R_3$ independently of one another are hydrogen, $C_1$-$C_8$alkyl or $C_1$-$C_8$alkyl which is substituted by one-COOR" group or by 1 to 3 OH groups, $C_2$-$C_8$hydroxyalkyl which is interrupted by one or more —O— groups, —($C_1$-$C_8$)alkylene-COO$^\ominus$, —($C_1$-$C_8$)alkylidene-COO$^\ominus$, —($C_2$-$C_8$)alkylene-SO$_3^\ominus$ or —($C_2$-$C_8$)alkylidene-SO$_3^\ominus$ each of which is substituted by one OH group, $C_3$-$C_5$alkenyl, $C_5$-$C_7$cycloalkyl, phenyl, tolyl, benzyl or glycidyl, or $R_1$, together with $R_2$ and if appropriate with $R_3$ and together with the N atom to which they are attached, form an N-heterocyclic radical which can contain 1-3 N atoms or one O atom as ring members, R" is hydrogen or $C_1$-$C_4$alkyl and X$^\ominus$ if not present in $R_1$, $R_2$, $R_3$ or $R_{33}$, is a colourless organic or inorganic anion, and $R_{23}$, $R_{24}$, $R_{25}$, $R'_{23}$, $R'_{24}$ and $R'_{25}$ are hydrogen, OH, halogen, $C_1$-$C_4$alkoxy, $C_1$-$C_4$alkyl, phenyl or a group of formula Ia where g is 1.

2. A recording material according to claim 1, wherein the compound of the formula VI corresponds to a compound of the formula VIa

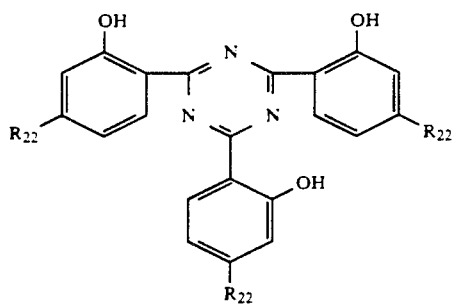
(VIa)
and $R_{22}$ is a group of the formula Ia in which $g=1$.
* * * * *

UNITED STATES PATENT AND TRADEMARK OFFICE
CERTIFICATE OF CORRECTION

PATENT NO. : 5,096,781

DATED : MARCH 17, 1992

INVENTOR(S) : ERIC VIEIRA, ET AL.

It is certified that error appears in the above-identified patent and that said Letters Patent is hereby corrected as shown below:

Column 40,

Claim 1, line 1, after "containing" insert -- a carrier and, --.

Signed and Sealed this

Fourteenth Day of September, 1993

Attest:

BRUCE LEHMAN

*Attesting Officer*     *Commissioner of Patents and Trademarks*